US006848451B2

United States Patent
Postal et al.

(10) Patent No.: US 6,848,451 B2
(45) Date of Patent: *Feb. 1, 2005

(54) DRIVE MECHANISM FOR OSCILLATORY ABRASION AND POLISHING TOOL

(75) Inventors: Robert T. Postal, Glen Cove, NY (US); Robert P. Wallace, Amawalk, NY (US)

(73) Assignee: Twist2It, Inc., Flushing, NY (US)

( * ) Notice: Subject to any disclaimer, the term of this patent is extended or adjusted under 35 U.S.C. 154(b) by 197 days.

This patent is subject to a terminal disclaimer.

(21) Appl. No.: 10/174,082

(22) Filed: Jun. 18, 2002

(65) Prior Publication Data

US 2002/0157680 A1 Oct. 31, 2002

Related U.S. Application Data

(63) Continuation of application No. 09/678,802, filed on Oct. 3, 2000, now Pat. No. 6,409,507, which is a continuation-in-part of application No. 09/288,764, filed on Apr. 8, 1999, now Pat. No. 6,247,931, which is a continuation-in-part of application No. 08/878,995, filed on Jun. 19, 1997, now Pat. No. 5,931,672.

(51) Int. Cl.[7] .............................................. A45D 29/14
(52) U.S. Cl. ..................................... 132/75.8; 451/162
(58) Field of Search ............................ 132/75.8; 74/54, 74/569; 433/118, 122, 125; 451/108, 121, 162, 163

(56) References Cited

U.S. PATENT DOCUMENTS

| 656,124 A | * | 8/1900 | Kinnison ................... 433/124 |
| 1,182,187 A | * | 5/1916 | McEldowney ........... 15/104.12 |
| 1,982,336 A | * | 11/1934 | Wiseman .................... 433/126 |
| 2,135,933 A | * | 11/1938 | Blair ............................ 601/89 |
| 2,389,232 A | * | 11/1945 | Conlon ........................ 91/279 |

Primary Examiner—Ralph A. Lewis
(74) Attorney, Agent, or Firm—Kirkpatrick & Lockhart LLP; Anthony H. Handal

(57) ABSTRACT

A transmission for changing rotary motion into angularly reciprocating motion and adapted to be mounted on the output end of a power unit of the type having a rotary drive output and used to drive a tool. The transmission is comprised of a support member, a driving resinous member supported by the support member for rotary motion, and a driven resinous member supported by the support member for reciprocating angular movement by the support member. The transmission subassembly is formed by the driving resinous member, driven resinous member and support member and adapted to be mounted on the output end of the power unit with a rotary drive output mechanically coupled to the driving resinous member. A driving cam surface is disposed on a portion of the driving resinous member. A driven cam surface is disposed on a portion of the driven resinous member. The driving cam surface is in contact with the driven cam surface during at least a portion of the cycle of rotation of the driving cam surface. The driven cam surface is configured and dimensioned to be driven by the driving cam surface in a positive angular direction during one part of the cycle and is driven by the driving cam surface in a negative angular direction during another part of the cycle. Angularly reciprocating motion is thereby imparted to the tool as the driving cam surface and driven cam surface engage each other. The tool is particularly advantageous when used in connection with motorized manicure tools, polishing devices, and dermabrasion devices.

12 Claims, 16 Drawing Sheets

U.S. PATENT DOCUMENTS

| | | | | |
|---|---|---|---|---|
| 2,400,912 A | * | 5/1946 | Britt | 433/82 |
| 2,451,706 A | * | 10/1948 | Aimes | 91/152 |
| 2,514,142 A | * | 7/1950 | Reid | 15/22.1 |
| 2,706,969 A | * | 4/1955 | Bannister et al. | 91/287 |
| 2,923,303 A | * | 2/1960 | Hundt | 132/75.8 |
| 3,769,707 A | * | 11/1973 | Condon | 433/82 |
| 4,099,448 A | * | 7/1978 | Young | 91/339 |
| 4,272,229 A | * | 6/1981 | Pape | 417/481 |
| 4,371,341 A | * | 2/1983 | Nakanishi | 433/118 |
| 4,408,623 A | * | 10/1983 | Murray | 132/73.6 |
| 4,460,341 A | * | 7/1984 | Nakanishi | 433/122 |
| 5,033,485 A | * | 7/1991 | Hauerwas et al. | 132/73.6 |
| 5,040,978 A | * | 8/1991 | Falcon et al. | 433/125 |
| 5,120,220 A | * | 6/1992 | Butler | 433/125 |
| 5,145,369 A | * | 9/1992 | Lustig et al. | 433/118 |
| 5,340,310 A | * | 8/1994 | Bifulk | 433/123 |
| 5,931,672 A | * | 8/1999 | Postal et al. | 433/118 |
| 6,247,931 B1 | * | 6/2001 | Postal et al. | 433/118 |
| 6,409,507 B1 | * | 6/2002 | Postal et al. | 433/118 |

* cited by examiner

Figue 26

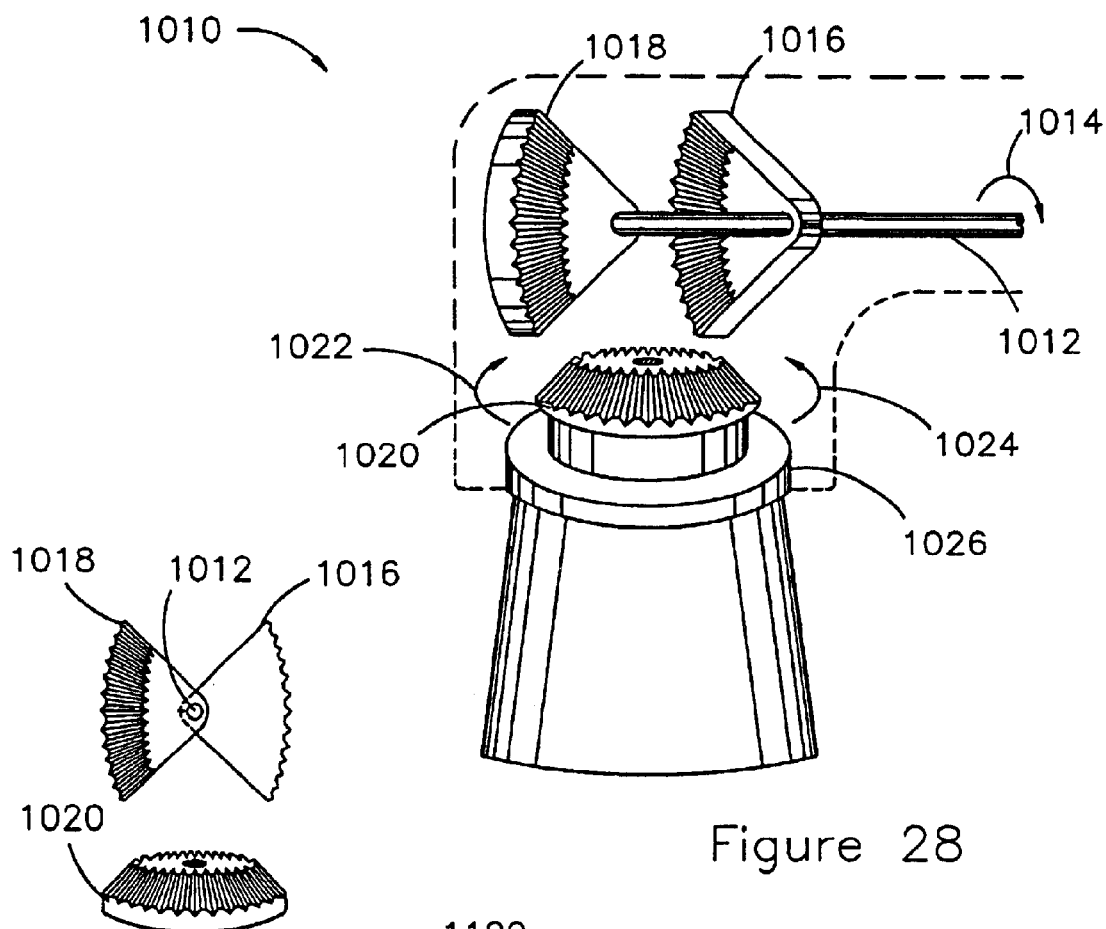
Figure 28
Figure 29
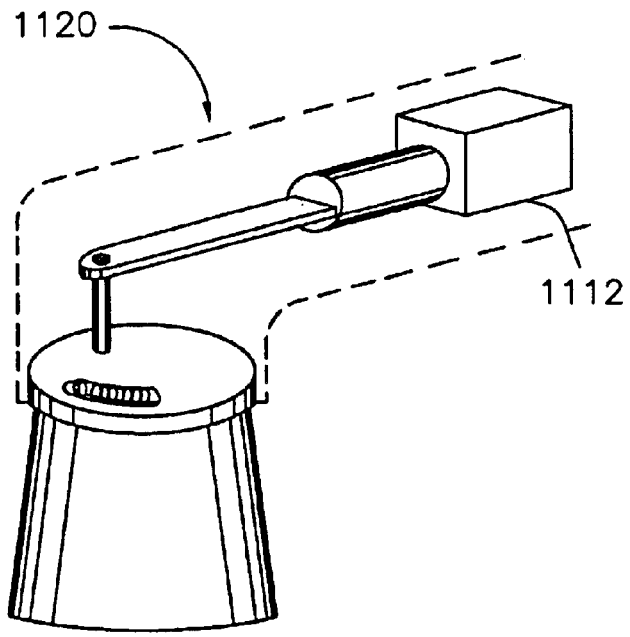
Figure 30

DRIVE MECHANISM FOR OSCILLATORY ABRASION AND POLISHING TOOL

CROSS-REFERENCE TO RELATED APPLICATIONS

This application is a continuation of Postal et al. U.S. application Ser. No. 09/678,802 filed Oct. 3, 2000 now U.S. Pat. No. 6,409,507 which is a continuation-in-part of Postal et al. U.S. application Ser. No. 09/288,764, filed Apr. 8, 1999 now U.S. Pat. No. 6,247,931 which is a continuation-in-part of Postal et al. U.S. application Ser. No. 08/878,995, filed Jun. 19, 1997, now U.S. Pat. No. 5,931,672. The disclosures of application Nos. 09/678,802, 09/288,764, and 08/878,995 and PCT/US01/30692 filed Oct. 2, 2001 are hereby incorporated herein by reference thereto.

STATEMENT REGARDING FEDERALLY SPONSORED RESEARCH OR DEVELOPMENT

Not Applicable

BACKGROUND OF THE INVENTION

1. Technical Field

The present invention relates to a tool assembly having a head that imparts oscillatory motion to a desired device coupled to the assembly. More particularly, the present invention relates to a drive mechanism for a tool assembly, the drive mechanism having a rotating drive shaft that engages a first end of a driven shaft to rotate the driven shaft in an oscillatory manner. The inventive tool assembly is particularly advantageous when used in connection with massaging, dermabrasion, nail buffing and sculpting, woodworking and polishing assemblies.

2. Description of the Related Art

Brushes have been used for many years to polish, clean and abrade a wide variety of substrates. These brush products typically have a plurality of bristles that contact the substrate. U.S. Pat. Nos. 5,152,917 and 5,304,223 (Pieper et al.) teach coated abrasive articles comprising precisely shaped abrasive composites bonded to a backing. The abrasive composites comprise binder and abrasive particles. The precisely shaped composites can be in the form of for example, pyramids, sawtooth grooves, or linear grooves. The maximum distance between corresponding points on adjacent composite shapes can be less than one millimeter. The coated abrasive of Pieper et al. can be made, for example, according to the following general procedure. First, a slurry containing abrasive grains and binder is introduced to a production tool. Second, a backing is introduced to the outer surface of the production tool such that the slurry wets the front side of the backing. Third, the binder is at least partially cured. Fourth, the production tool is removed from the backing.

U.S. Pat. Nos. 5,174,795 and 5,232,470 (Wiand) teach a planar abrasive article comprising a sheet portion with a plurality of protrusions extending therefrom. Abrasive particles are homogeneously dispersed throughout the moldable material comprising the article. Wiand teaches one embodiment having short protrusions extending 1.6 mm (0.063 in) from the backing and having a 3.2 mm (0.125 in) diameter, and another embodiment having short protrusions extending 1.3–1.5 mm (0.05–0.06 in) from the backing and having a 1.3 mm (0.05 in) diameter.

In recent years it has become fashionable for women to buff their fingernails to a shine for cosmetic reasons, particularly in the case where it is decided that the fingernails should remain natural color. A wide variety of attempts have been made for the provision of motor-powered abrading and polishing devices for fingernails and toenails. These have included both manipulable or portable units employing rotary abrading units and larger, static or table-type units.

Prior forms of small, rotary manicuring units have employed small, high speed motors in order to achieve the desired compactness. Since motor torque is a function of the size of the motor and, especially, since the surface speed of a rotating unit is directly related to the tool diameter, for a given speed, the tools or abrasive bits of such prior units typically have been limited in diameter to less than one-half inch. Currently in the nail manicure field a rotary style drilling device is used to trim nails and acrylic extenders.

These prior units have not been well accepted by consumers for several reasons.

The very high speeds and the sensible torque reaction have made it quite difficult for an untrained individual to control such units. The tendency is for the abrasive bit to recoil or to run itself away from the nail. This made it almost necessary to provide additional guidance for the controlling hand, such as by the use of a second hand as an additional guiding means. While this is feasible when the units are used by a second person, it is clearly unsuitable when it is desired to use the unit for self-manicure.

Using the rotating device with a bur (drill bit) can be a dangerous device when used improperly. These high-speed, small-diameter bits tend to groove or to "scallop" the nail if they are presented against the nail with too much force or for too long a time. Therefore, any distraction or inattention frequently would result in the formation of a small-diameter arc-shaped deformation of the nail, in contrast to the desired sculpturing being attempted. In the course of the invention, it has been discovered that many accidents occur namely by cutting into the cuticle area, which can lead to some serious infections. In addition it has also been discovered that fingernail/cuticle infections are on the rise because of improper use of these polishing/sanding drills and the fact that these drills are rarely sterilized properly.

BRIEF SUMMARY OF THE INVENTION

It is therefore an object of the present invention to provide a disposable tool assembly having a driving mechanism that imparts oscillatory rotary motion to a device mounted on the assembly and to achieve this with a structure that can be economically, and reliably implemented in plastic to allow for disposability and the attendant avoidance of the spreading of infection.

It is a related object of the present invention to provide a driving mechanism having a drive shaft and a driven shaft each having driving surfaces shaped to engage each other and ride along each other such that rotation of the drive shaft causes oscillatory rotation of the driven shaft.

It is a further object of the present invention to provide a tool assembly having driving and driven elements that are stabilized with respect to each other against relative movement in a given direction.

It is another object of the present invention to provide an assembly having a drive shaft that is coupled to a driven element such that the drive shaft imparts only oscillatory motion to the driven element without also imparting axial motion to the driven element.

These and other objects of the present invention are accomplished in accordance with the principles of the present invention by providing a tool assembly having a rotating drive shaft that engages a driven shaft to impart oscillatory rotary motion to the driven shaft. The drive shaft and driven shaft are positioned transverse to each other. The drive shaft has a driving surface at its distal end that is shaped to engage a driven surface on a side of the driven shaft adjacent the drive shaft. Because of the manner in which the distal end is shaped, a stud or guide pin, such as used in the prior art, is no longer needed. Specifically, the driving surface is a cutaway, curved portion of an enlarged end of the drive shaft, and the driven surface is a cut-away side portion of the driven shaft. The cut-away portions of each shaft are shaped to inter-engage with substantially no play therebetween such that they are in continuous contact during rotation of the driving shaft. Because of the shapes of the cut-away portions, rotation of the driving shaft causes oscillatory rotation of the driven shaft.

The drive shaft and driven shaft are positioned within a housing. In order to prevent relative movement of the shafts with respect to the housing, a plurality of locking mechanisms are provided. First, the drive shaft is provided with a longitudinally extending pin aligned with the rotation axis of the drive shaft. The driven shaft is provided with a slot through which the pin is passed. The slot is shaped so that oscillatory rotation of the driven shaft is not inhibited by the pin, yet axial movement of the driven shaft along its rotation axis is prevented. Another locking mechanism for the drive shaft is provided in the form of at least one flange extending radially from the drive shaft and engaging a radially inwardly extending flange on the inner surface of the housing. The driven shaft is provided with a rearwardly positioned pin that fits within a bore in the housing to lock the driven shaft in the desired position for oscillation.

BRIEF DESCRIPTION OF THE SEVERAL VIEWS OF THE DRAWING

These and other features and advantages of the present invention will be readily apparent from the following detailed description of the invention, the scope of the invention being set out in the appended claims. The detailed description will be better understood in conjunction with the accompanying drawing, wherein like reference characters represent like elements throughout the various views of the drawing and:

FIG. 26 is a perspective view of a plastic driving mechanism of the tool assembly incorporating a multiple cam driving mechanism;

FIG. 28 is a perspective view of a plastic driving mechanism of the tool assembly incorporating a multiple gear driving mechanism;

FIG. 29 is a side view of the multiple gear driving mechanism;

FIG. 30 is a perspective view of a plastic driving mechanism of the tool assembly incorporating an electromechanical operator;

DETAILED DESCRIPTION OF THE PREFERRED EMBODIMENTS

Figure 1:
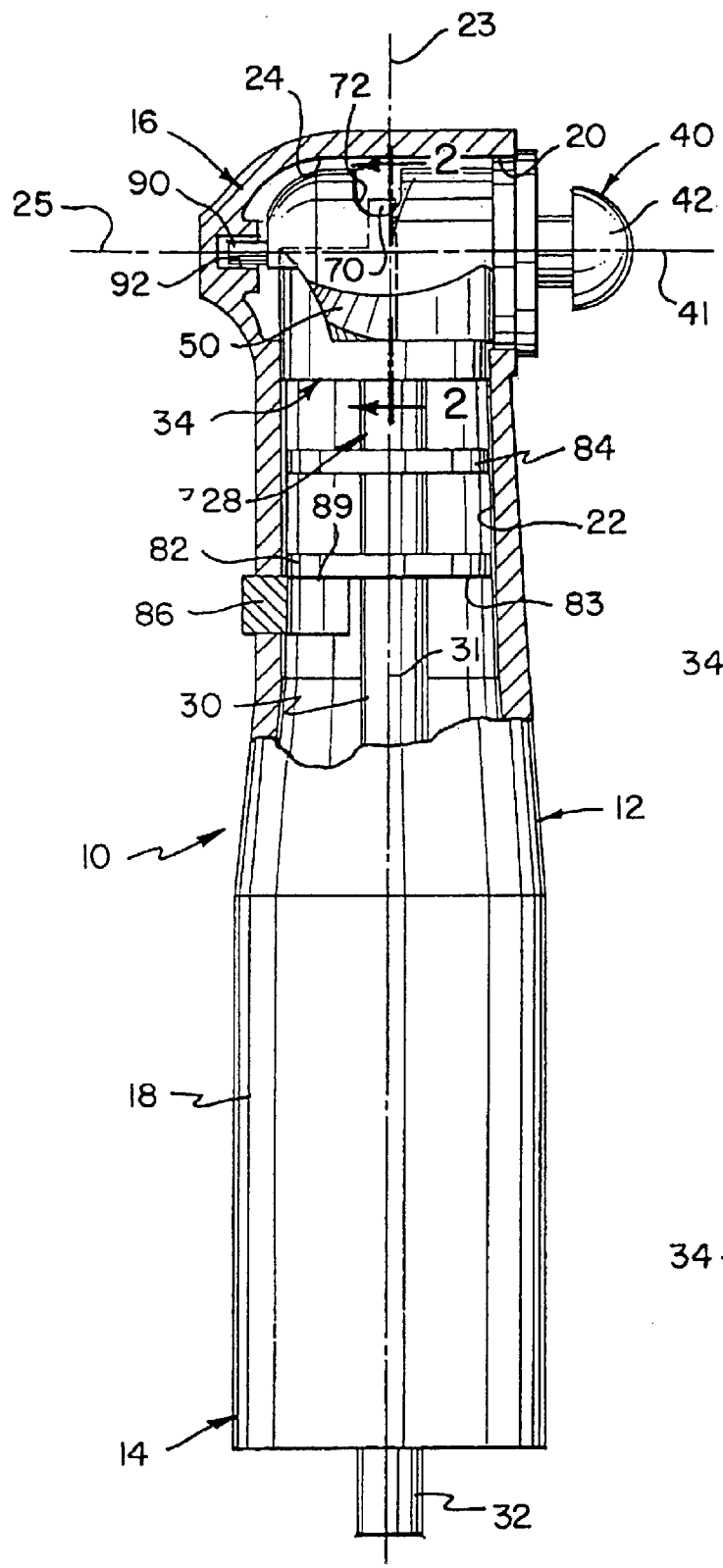
FIG. 1 is an elevational, partially cut-away view of a tool assembly formed in accordance with the principles of the present invention.
Figure 2A:
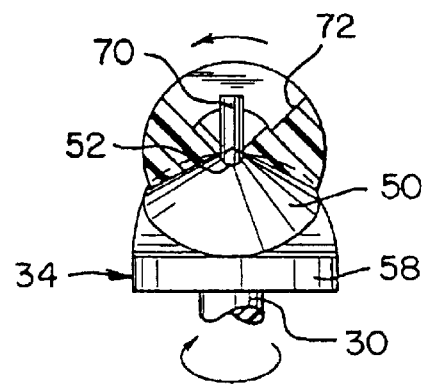
FIG. 2A is a cross-sectional view of the distal end of the tool assembly of FIG. 1 along line 2—2, with the driven shaft in the rest position.
Figure 2B:
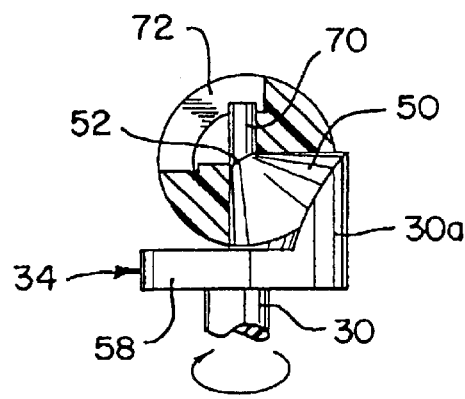
FIG. 2B is a cross-sectional view of the distal end of the tool assembly of FIG. 1 along line 2—2 with the drive shaft rotated 90° from the position shown in FIG. 2A.
Figure 3:
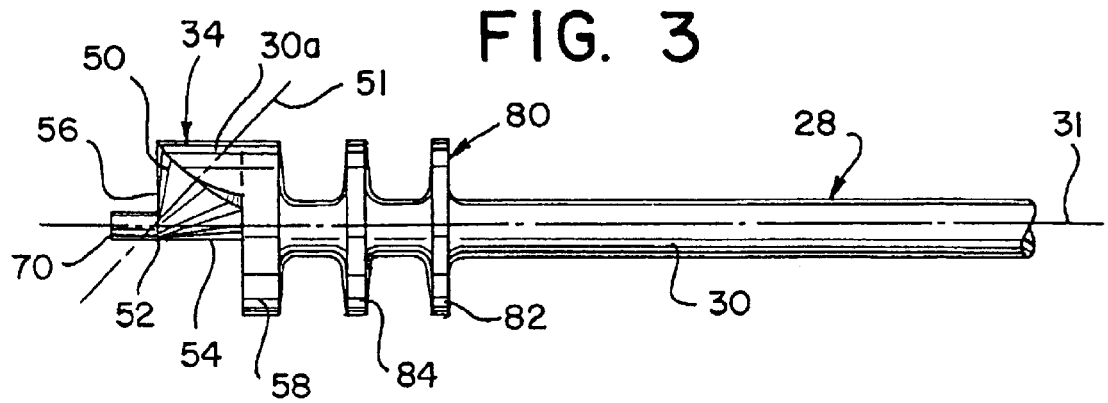
FIG. 3 is an elevational view of a drive shaft formed in accordance with the principles of the present invention.
Figure 4:
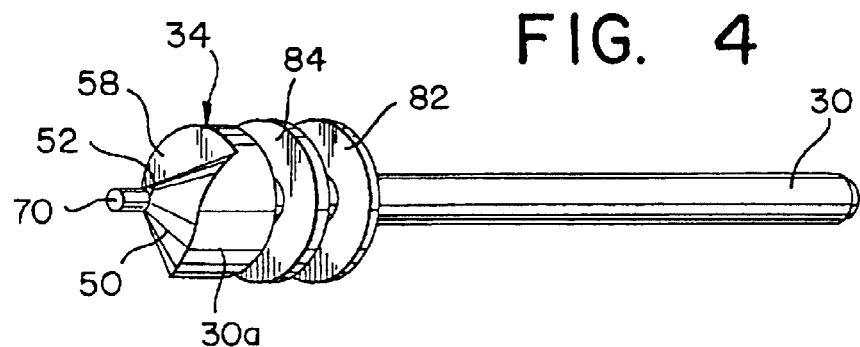
FIG. 4 is a perspective view of the drive shaft of FIG. 2.
Figure 5:
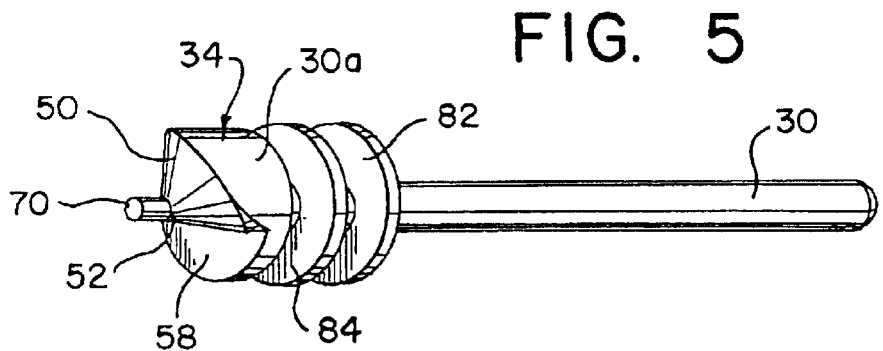
FIG. 5 is a perspective view of the drive shaft of FIGS. 3 and 4, rotated to another position.
Figure 6:
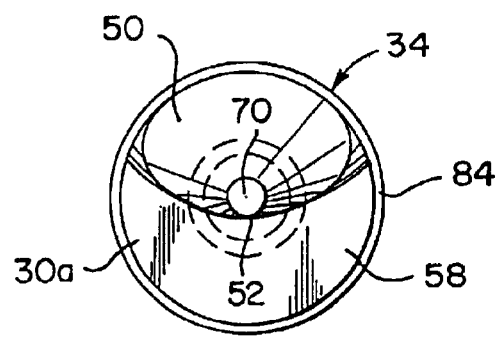
FIG. 6 is an end view of the drive shaft of FIG. 3.

A tool assembly 10, formed in accordance with the principles of the present invention, is shown in FIG. 1. Tool assembly 10 includes a housing 12 having a proximal end 14 and a distal end 16, with main body portion 18 extending therebetween. Proximal end 14 is coupled to a tool hand piece (not shown) known in the art. Distal end 16 has a side opening 20 at which a desired device (not shown) is coupled. However, the preferred embodiment of the tool assembly shown in the Figures is a polishing brush which would be appropriately adjusted for use in buffing nails, or for polishing shoes or furniture and the like. Alternative embodiments replacing the brush with an abrasive surface are also contemplated. It will be understood that any appropriate tool piece known in the art may be used.

Housing 12 is hollow such that first and second channels 22, 24 are formed therein for housing driving mechanism 28. First, longitudinal channel 22 is formed within main body portion 18 and extends from proximal end 14 to distal end 16 along longitudinal axis 23 of main body portion 18. Second, transverse channel 24 extends across the distal end 16 of housing 12 and opens at side opening 20 of housing 12. Longitudinal axis 25 of transverse channel 24 is transverse and preferably substantially perpendicular to longitudinal axis 23 of housing 12.

Driving mechanism 28 includes a drive shaft 30 and a driven shaft 40. Drive shaft 30 is housed in first channel 22 and has a longitudinal rotation axis 31 which preferably corresponds to longitudinal, axis 23 of main body portion 18. A proximal end 32 of drive shaft 30 preferably extends beyond proximal end 14 of housing 12 for connection to a rotary unit (not shown), such as a motor, for rotating drive shaft 30, as known in the art. Distal end 34 of drive shaft 30 extends toward, and preferably partially into, second channel 24. Driven shaft 40 is housed in second channel 24 and has a longitudinal rotation axis 41 which preferably corresponds to longitudinal axis 25 of transverse channel 24. Driven shaft 40 preferably has a coupling element 42 extending therefrom through side opening 20 and out of housing 12. A desired device, such as a brush or abrasion head may be selected and coupled to coupling element 42.

Drive shaft 30 and driven shaft 40 have driving surfaces that are shaped to interengage each other to result in a camming action that translates rotation of drive shaft 30 into oscillatory rotation of driven shaft 40 substantially without play between the driving surfaces, as will now be described. As shown in FIGS. 2A, 2B, and 3–6, drive shaft 30 has a drive surface 50 (which functions essentially as a cam) at distal end 34. Preferably drive surface 50 has a substantially conical cam surface, with cone axis 51 being at a preferably 45' angle with respect to rotation axis 31, as may be observed in FIG. 3. The conical shape is readily appreciated with reference to FIGS. 2A, 2B, and 3–6. The tip 52 of conical drive surface 50 preferably is aligned with rotation axis 31 so that a longitudinal surface portion 54 of conical surface 50 is aligned with rotation axis 31 and a transverse surface portion 56 of conical surface 50 is substantially perpendicular, i.e., at a 90' angle, with respect to rotation axis 31 and thus with respect to longitudinal surface portion 54. As may be seen in FIGS. 2B and 3–6, conical surface 50 is formed to one side of rotation axis 31. Conical surface 50 may be formed by cutting away a portion of an enlarged region 30a of shaft 30, thus leaving a flange-like section 58 at distal end 34.

Figure 7:
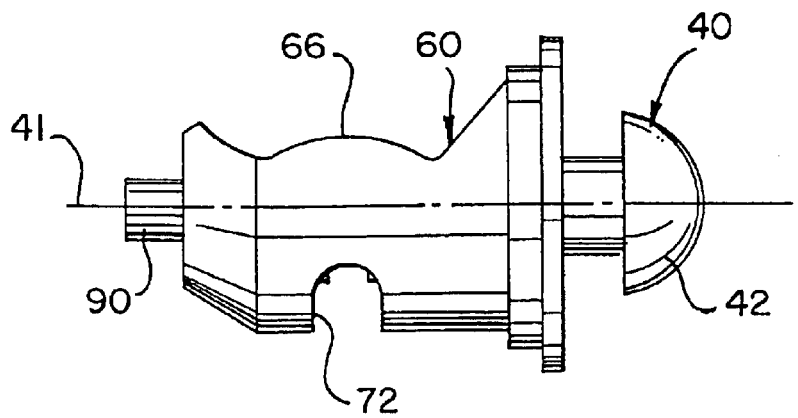
FIG. 7 is an elevational view of a driven shaft formed in accordance with the principles of the present invention.

Driven shaft 40 (which essentially functions as a cam follower), shown in isolation in FIGS. 7–10, has a driven surface 60 along its side (i.e., extending along rotation axis 41 of driven shaft 40). The elevational view of FIG. 7 is similar to the view of driven shaft 40 in FIG. 1, except that driven shaft 40 is shown with driven surface 60 facing upward, rather than downward as in FIG. 1. Typically, driven surface 60 is formed as a cut-away portion of a side of driven shaft 40. Driven surface 60 has alternating hills 62 and valleys 64. Preferably, two hills 62 are provided opposite each other with a valley 64 between adjacent, juxtaposed sides of opposed hills 62, thus spacing hills 62 apart. Viewed another way, the upwardly extending sides of the opposite valleys 64 are joined to form hills 62. Hills 62 and valleys 64 are shaped to conform-n to the shape of drive surface 50 such that drive surface 50 is in continuous contact with driven surface 60 with substantially no play therebetween as drive shaft 30 rotates during operation of tool assembly 10. Specifically, valleys 64 of driven surface 60 are conically cut-away such that conical drive surface 50 may be engaged therewith such that transverse surface portion 56 and distal surface portions adjoining transverse surface portion 56 of conical drive surface 50 are in close contact with the surfaces of a valley 64. Because opposite sides of conical drive surface 50 are at an approximately 90' angle with respect to each other and valleys 64 are shaped to conform to conical drive surface 50 with hills 62 formed at the sides of valleys 64, peaks 66 of hills 62 are preferably also at an approximately 90' angle with respect to each other. The contour of driven surface 60 may be better understood from a review of the elevational views of FIGS. 8 and 10.

The camming action of the present invention, which permits rotation of drive shaft 30 to cause oscillatory rotation of driven shaft 40 as a result of the interaction of the shapes of driving surfaces 50, 60, will now be described. When drive surface 50 engages a valley 64 of driven surface 60, driven shaft 40 is in a rest position (i.e., driven surface 60 completely faces drive surface 50 and proximal end 14 of housing 12, rather than a side of housing 12, as shown in FIG. 1). As drive shaft 30 rotates about rotation axis 31, drive surface 50 moves along driven surface 60 until drive surface 50 engages a hill 62. As described above, and as may be seen in FIG. 8, the peaks 66 of opposite hills 62 are positioned substantially 180' apart with the bottoms 65 of valleys 64 approximately 90' from each peak 66. Thus, when drive surface 50 has rotated 90' from a rest position in contact with valley 64 (such as shown in cross-sectional view 2A), drive surface 50 comes into contact with adjacent hill 62. When transverse surface portion 56 of drive surface 50 contacts peak 66 of an adjacent hill 62, peak 66 is also transverse to rotation axis 31 such that driven shaft 40 is rotated 90' about its rotation axis 41 from its rest position. It is noted that peaks 66 are at an approximately 90' angle with respect to each other, as may be seen in FIG. 2B, and longitudinal and transverse portions 54, 56 of drive surface 50 are also at an approximately 90' angle with respect to each other, as may be appreciated with reference to FIGS. 1, 2B, and 3. Thus, when transverse portion 56 of drive surface 50 contacts a peak 66 to rotate driven shaft 40, longitudinal portion 54 is in contact with the opposite peak 66. As drive surface 50 continues to be rotated upon rotation of drive shaft 30, drive surface 50 contacts the next valley 64 (opposite the first mentioned valley), returning driven shaft 40 to the rest position. Further rotation of drive shaft 30 brings drive surface 50 into contact with the next hill 62 (opposite the first-mentioned hill), thereby rotating driven shaft 40, in the same manner as described above but in the opposite direction, 90' about rotation axis 41. Thus, driven shaft 40 oscillates a total of 90', performing a quarter turn in opposite directions from a rest position.

Figure 8:
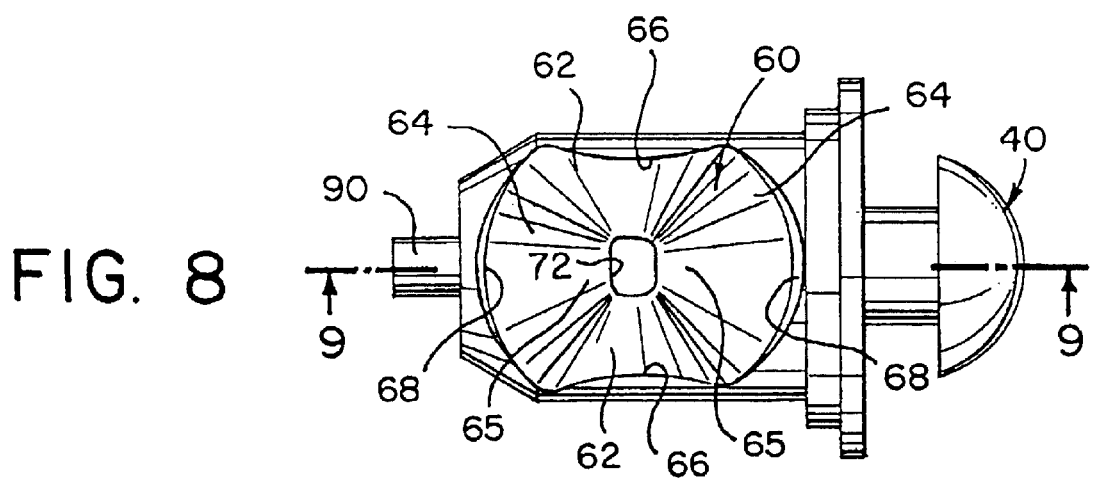
FIG. 8 is a plan view of the driven shaft of FIG. 7.
Figure 9:
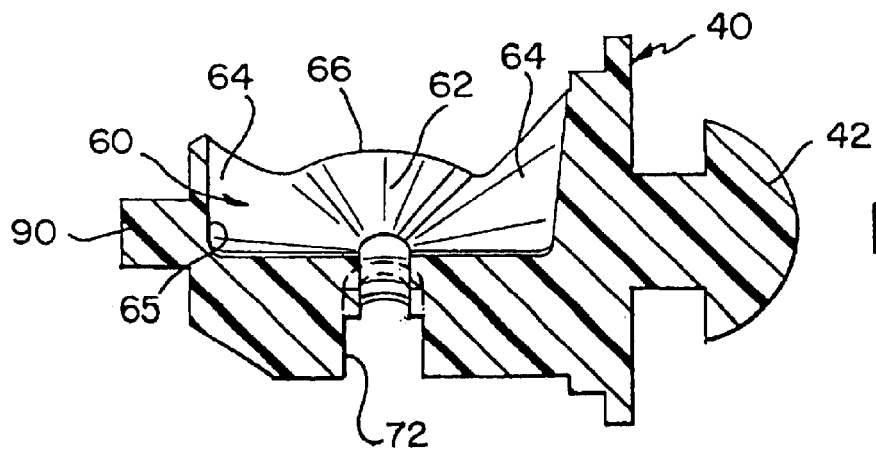
FIG. 9 is a cross-sectional view along line 9—9 of the driven shaft of FIG. 8.
Figure 10:
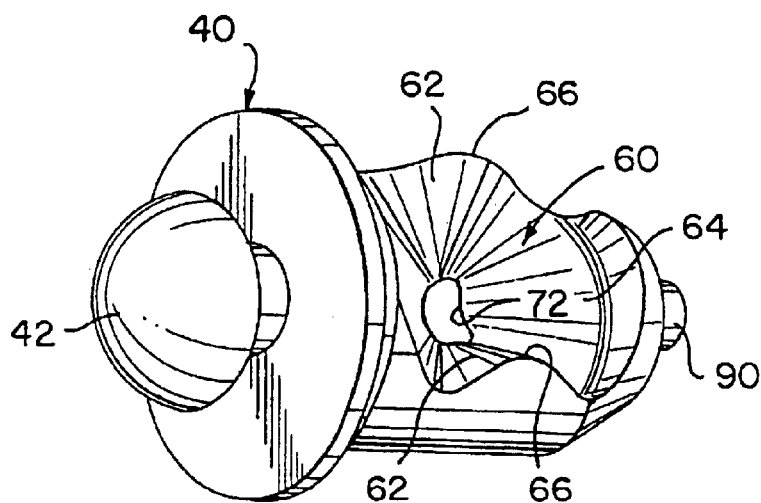
FIG. 10 is a perspective view of the driven shaft of FIGS. 7–9.
Figure 11:
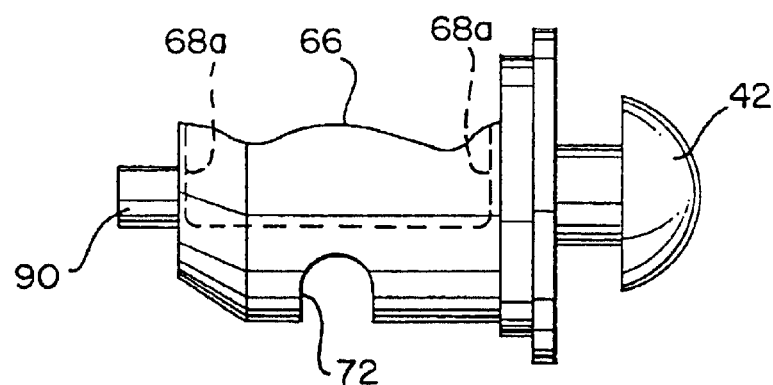
FIG. 11 is an elevational view of a driven shaft similar to that of FIG. 7 but with straight transverse walls of the driven surface.
Figure 12:
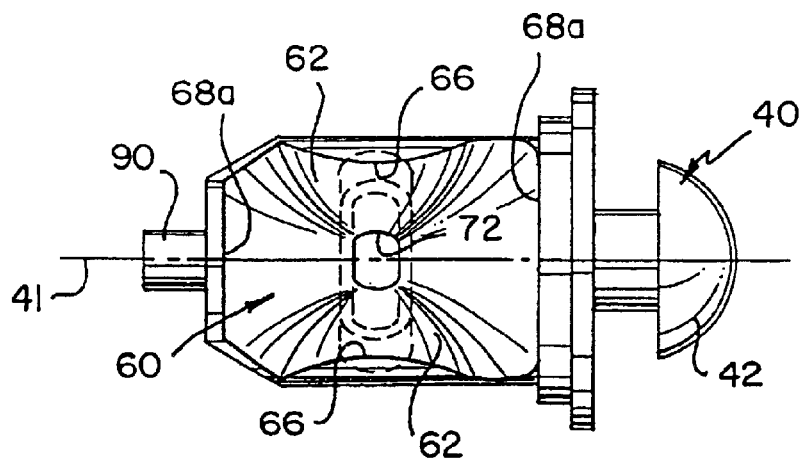
FIG. 12 is a plan view of the driven shaft of FIG. 11.

As may be seen in the plan view of FIG. 8, transverse side walls 68 of driven surface 60 are curved. However, in order to provide greater clearance between side walls 68 and drive shaft 30 (particularly the outer walls of enlarged region 30a extending substantially parallel to rotation axis 31) substantially straight side walls 68a may, instead, be provided, as shown in FIGS. 11 and 12. Straight side walls 68a extend, from the widest portions of valleys 64, along the periphery of driven surface 60 substantially perpendicular to rotation axis 41 of driven shaft 40.

Because typically only oscillatory rotation, without axial reciprocation, of driven shaft 40 is desired, it is desirable to fix drive shaft 30 with respect to driven shaft 40. In accordance with the principles of the present invention, drive shaft 30 is provided with an axially extending pin 70 that is substantially aligned with rotation axis 31. Driven shaft 40 is provided with a corresponding slot 72, which may extend completely through driven shaft 40, as shown in FIGS. 2A, 2B, and 7–10. It will be understood that slot 72 need not extend completely through driven shaft 40, as shown, as long as sufficient engagement between pin 70 and slot 72 is achieved. The axial extent of slot 72 along rotation axis 41 of driven shaft 40 is selected to provide a substantially close fit with the diameter of pin 70 to prevent axial reciprocation of driven shaft 40 along axis 41. However, the transverse extent of slot 72 (in a direction perpendicular to axis 41) is selected such that 90' rotation of driven shaft 40 with respect to drive shaft 30 (45' rotation of driven shaft 40 in each direction from the rest position) is permitted without causing shifting of either shaft 30, 40 from respective axes 23, 25 of housing 12.

In order to prevent movement of shafts 30, 40 from their proper positions within channels 22, 24 of housing 12, position retaining elements are provided as follows. In order to prevent axial shifting of drive shaft 30 along axis 31, drive shaft 30 is provided with at least one radially extending stop flange 80. As shown in FIGS. 1 and 3–5, preferably a proximal flange 82 and a distal flange 84 are provided. Flange 58 may also be considered to perform the same function as that of flanges 82 and 84 and thus may be considered a stop flange 80 as well. Housing 12 is provided with a latch 86 (inserted after assembly in order to maintain the parts of tool assembly 10 in place) having a position retaining surface 89 extending radially inwardly from the walls of channel 22. Position retaining surface 89 is positioned adjacent and along a retaining surface 83 of proximal flange 82 to prevent proximal axial movement of drive shaft 30 towards proximal end 14 of housing 12. Additional position retaining surfaces may be provided extending radially inwardly from the inner walls of channels 22 to engage proximal position retaining surfaces on flanges 58 and 84 as well. It will be understood that the position retaining surfaces formed on housing 12 need, not be in the form of a latch, but may be in any other form, such as a radially inwardly extending shoulder, that provides a sufficient surface area for engaging a proximal face of at least one of the flanges 80 on drive shaft 30. Moreover, the position retaining surfaces on housing 12 must be securely fixed to housing 12 along axis 23 to prevent movement of drive shaft 30 along axis 23.

In order to secure axial alignment of driven shaft 40 with axis 25, a positioning pin 90 may be provided at a rear, inner end of driven shaft 40 to fit within bore 92 at a rear end of channel 24 of housing 12, as shown in FIG. 1. Pin 90 not only serves to maintain proper alignment of driven shaft 40 during use, but also facilitates alignment of driven shaft 40 in housing 12 during assembly.

Preferably, to assemble tool assembly 10, driven shaft 40 is first positioned in housing 12, with pin 90 fitting within bore 92 such that rotation axis 41 of driven shaft 40 is properly aligned with longitudinal axis 25 of channel 24. Driven shaft 40 is rotated into its rest position such that driven surface 60 faces proximal end 14 of housing 12. Drive shaft 30 may then be inserted into channel 22, with pin 70 extending into slot 72 of driven shaft 40. Latch 86 then is positioned such that position retaining surface 89 faces position retaining surface 83 to maintain drive shaft 30 in its proper position along longitudinal axis 31 of channel 22. Tool assembly 10 then is ready for coupling with the desired hand piece.

Figure 13:
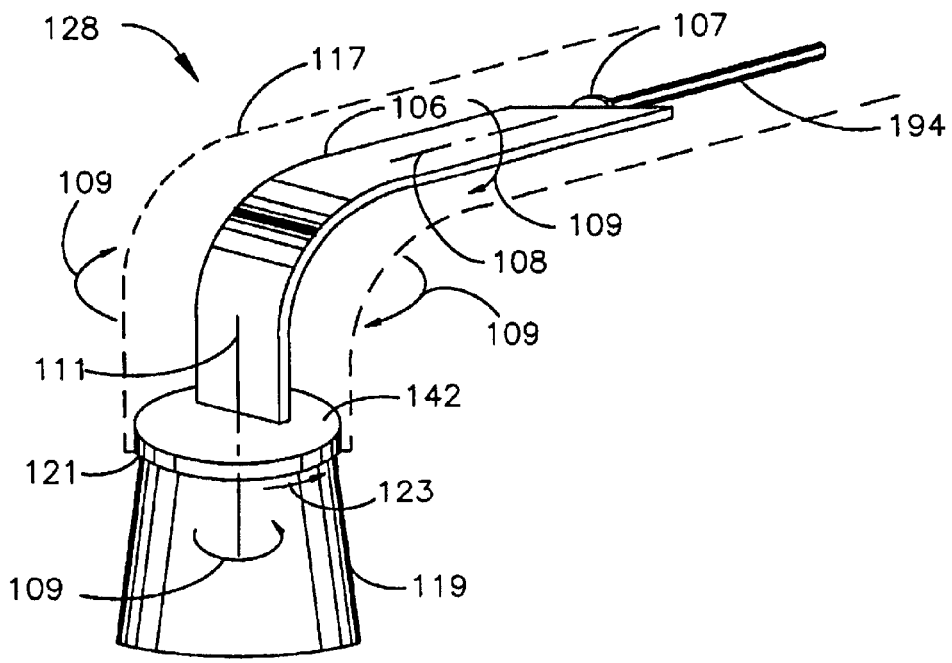
FIG. 13 is a perspective view of a plastic driving mechanism of the tool assembly incorporating a flexible driving member.

An alternative embodiment of the present invention is illustrated in FIG. 13. In this embodiment, the inventive plastic driving mechanism 128 is driven by a rotating member 194, which serves as a source of rotary input power. Rotating member 194 is a simple elongated driving shaft, of the same configuration as the driving shaft in a conventional objects, and thus, like the other inventive embodiments of the invention may be easily substituted in existing apparatus in wide use. Rotating member 194 is coupled to a flexible driving member 106 by any suitable coupling 107. During use, flexible driving member 106 is rotated in the direction indicated by arrows 109. The part of flexible driving member 106 closer to rotating member 194 rotates along a horizontal longitudinal oscillatory axis 108. Similarly, the distal portion of flexible driving member 106 rotates along a vertical oscillatory axis 111.

In accordance with this embodiment of the invention, flexible driving member 106 is maintained in a curved configuration. As can be seen in FIG. 13, flexible driving member 106 has a thickness 113 which is much smaller than its width 115. Because of the flexible driving member 106 is maintained in a curved configuration as illustrated in FIG. 13, rotation of the proximal portion of flexible driving member 106 at a constant speed causes a snap in the angular rotation of the distal end of flexible driving member 106.

This irregularity in angular speed amounts to a sort of stall during which a surface has an opportunity to resume an unstressed configuration. In many respects, the effect is similar to that achieved by the reciprocating motion of the attachment, which stresses the surface in one direction, then reverses direction, relieving the stress and lessening the likelihood of damage that would be more likely if one continued to apply stress and high-speed in one direction, as would be the case in the typical rotary drive mechanism.

Flexible driving member 106 is maintained in the curved configuration illustrated in FIG. 13 by housing, the same as in a curved tubular housing 117, which is illustrated in dashed lines in FIG. 13. More particularly, it is noted that in accordance with this embodiment of the invention, a brush head 119, which functions as a scrubbing surface and is of conventional design snaps onto a plastic support member 142. Plastic support member 142 is mounted for rotation within a secular mouth 121, which is configured to receive the disk shaped top of member 142, thus securely holding member 142 and allowing only rotation in the direction illustrated by arrow 123, in response to power input to the system by rotary member 194.

The intermittent nature of the motion in the embodiment illustrated in FIG. 13 may be improved by introducing a measure of friction between member 142 and mouth 121.

Figure 14:
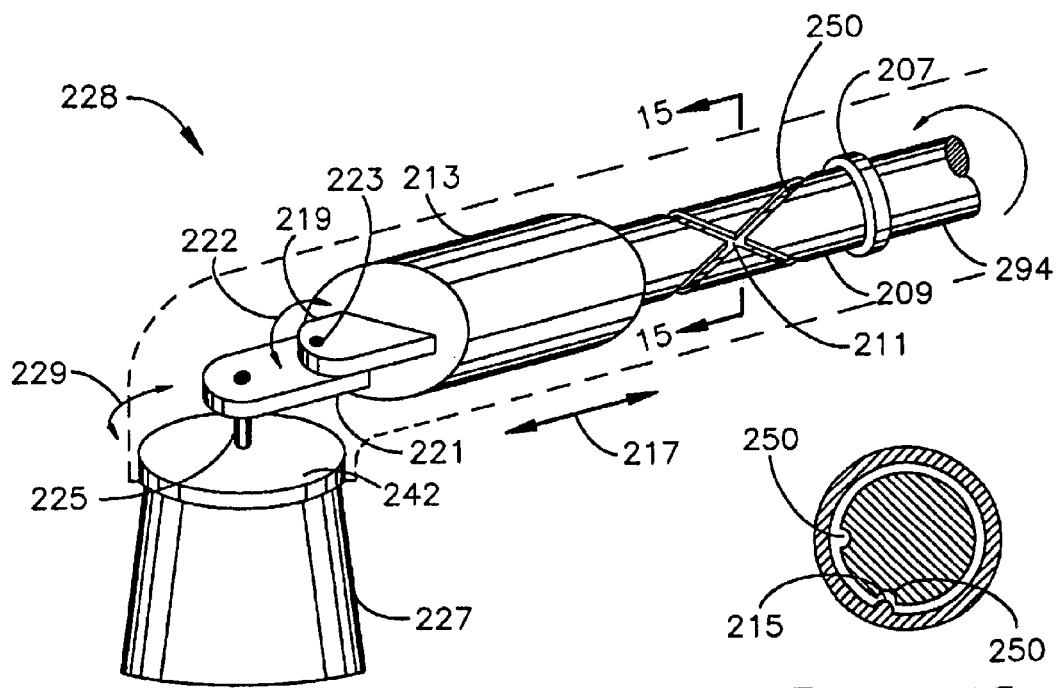
FIG. 14 is a perspective view of a plastic driving mechanism of the tool assembly incorporating a cylindrical driving member.
Figure 15:
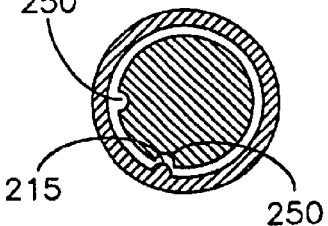
FIG. 15 is a cross-sectional view of the tool assembly of FIG. 14 along lines 15.

FIGS. 14 and 15 show an alternative embodiment of the inventive plastic driving mechanism 228. FIG. 14 is partially in exploded perspective as will be apparent from the following description. In this embodiment, plastic driving mechanism 228 is driven by a rotary input 294, of the type conventionally incorporated in a tool power source used to power a similar instrument. The output of rotary input 294 is coupled by a coupling mechanism 207 to a cylindrical driving member 209. Cylindrical driving member 209 defines a drive surface 250 comprising a figure-eight shaped groove. As can be seen in FIG. 14, this groove extends around cylindrical driving member 209 twice, crossing over itself at point 211 to define the figure-eight shape. For the sake of clarity of illustration, cylindrical driving member 209 is shown outside of sleeve 213. During operation, cylindrical driving member 209 is positioned within sleeve 213. Sleeve 213 has secured within it a cam following nub 215 which is positioned within groove-shaped drive surface 250, as illustrated in FIG. 15, during operation of the inventive plastic driving mechanism 228.

As can be seen from FIGS. 14 and 15, as cylindrical driving member 209 is rotated, because it is fixed in position within a suitable housing structure, it tends to pull sleeve 213 in a reciprocating motion along the axial direction as illustrated by arrow 217. This reciprocating motion is coupled to support 219. A drive member 221 is mounted for rotary movement in the directions of arrow 222 on support 219 by a shaft 223. Finally, brush head support 242 is coupled by a shaft 225 to drive member 221. As cylindrical driving member 209 is rotated in the direction indicated by arrow 205, nub 215 is pulled in the directions indicated by arrow 217, resulting in identical movement by the sleeve 213. This reciprocating movement is coupled to shaft 225 causing brush head support 242 and brush head 227 to reciprocate in the directions indicated by arrow 229 and achieve the desired action of cleaning the object without damage to the gums.

Figure 16:
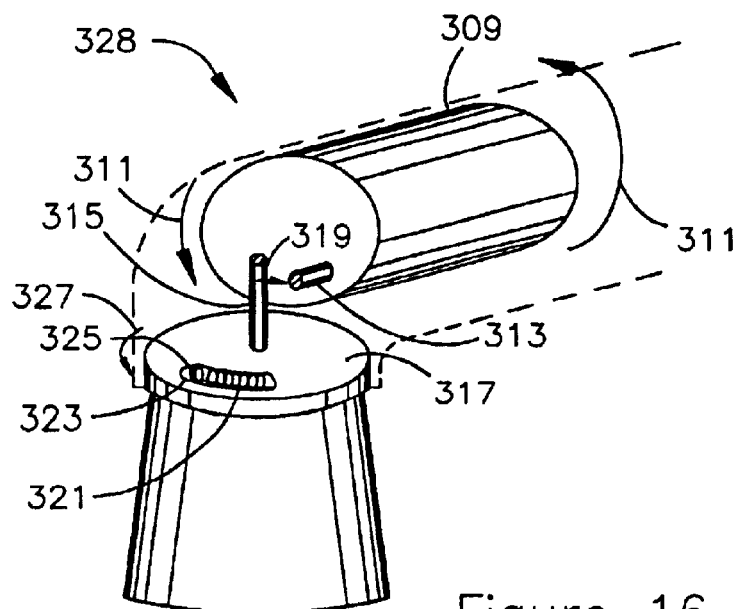
FIG. 16 is a perspective view of a plastic driving mechanism of the tool assembly incorporating a cylindrical driving member with shaft.

Referring to FIG. 16, yet another inventive plastic driving mechanism 328 for achieving reciprocating motion is shown. Generally, in this embodiment, the brush head is supported for rotary movement in a housing in much the same manner of the embodiments previously described. Rotary motion is converted into a periodic push which rotates the brush head against the support. When the push is released, the brush head snaps back into its original position.

More particular, cylindrical driving member 309 is rotated in the direction indicated by arrow 311. Rotation of cylindrical member 309 results in shaft 313 moving in a circular path. Shaft 313 is secured to cylindrical member 309. Periodically, shaft 313 bears against a shaft 315 which is secured to the brush head 317.

When shaft 313 bears against shaft 315 on brush head 317, it moves shaft 315 and rotates brush head 317 in the direction indicated by arrow 319. When this occurs, the spring 321 in a groove 323 in brush head 317 is compressed by a stock 325 which is rigidly secured with respect to housing 327 within which the drive member as illustrated in FIG. 16 is contained. As shaft 313 continues to move in a circular path, eventually it is rotated away from shaft 315, releasing shaft 315 and allowing spring 321 to expand, driving brush head 317 in the direction of arrow 327, thus resulting in reciprocating movement.

Figure 17:
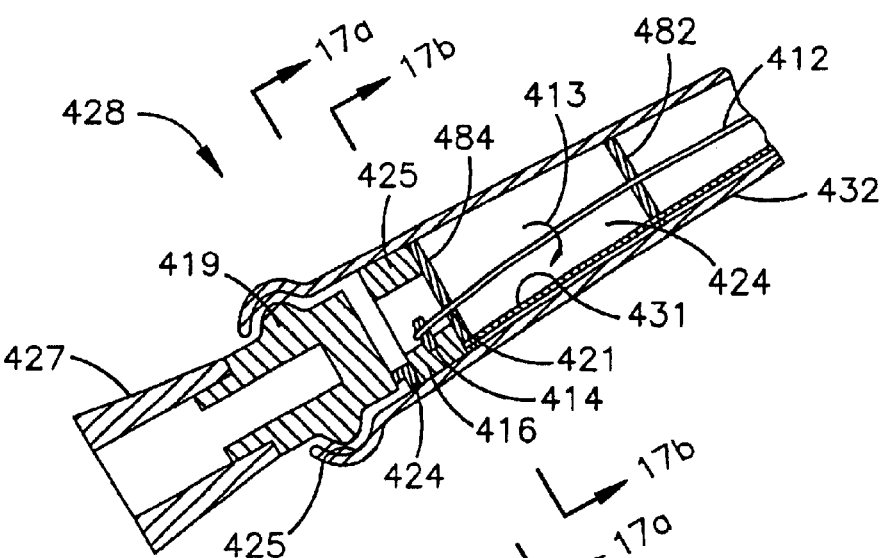
FIG. 17 is a perspective view of a plastic driving mechanism of the tool assembly incorporating multiple cam driving mechanism.
Figure 17A:
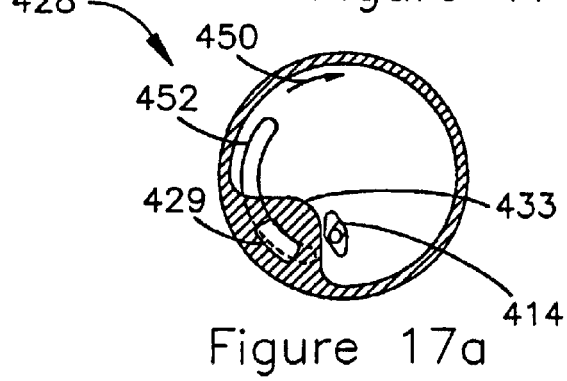
Figure 17B:
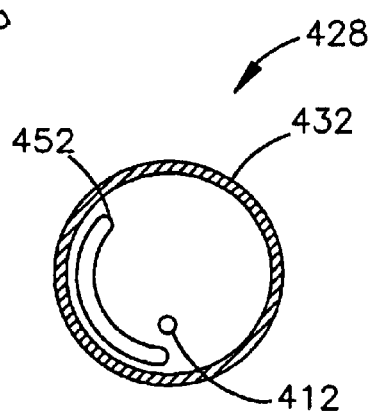

Referring to FIGS. 17a–17c, yet another inventive plastic driving mechanism 428 for achieving reciprocating movement in a brush head is illustrated. Here the driving mechanism 428 is driven by a drive shaft 412 with rotary motion in the direction of arrow 413. At the end of drive shaft 412 is a driving cam 414. Drive shaft 412 is retained in position in a space 424 in housing 432 by a disc shaped position retaining element 482 having a centered hole 415 as shown in FIG. 17a, and a second disc shaped position retaining element 484 having an off-centered hole 421 to accept drive shaft 412 as shown in FIG. 17b. The proximal end of drive shaft 412 extends partially through a circumferential shaped driven cam 416 mounted for rotation in housing 432. Brush head support 419 can be detachably mounted into housing 432 by an annular ridge 422 Ridge 422 snappingly engages an annular groove 425.

A coupling element 429 connects circumferential shaped driven cam 416 to support 419 in housing 432. A spring like member 431 springingly positions cam 416 in housing 432.

Rotary motion is converted into reciprocating motion when driving shaft 412 rotates, causing the driving cam 414 to bear against circumferential shaped driven cam 416 in the direction as shown by arrow 450. As shown in FIG. 17c, the result is to impart the forward portion of a reciprocating motion to coupling member 429 which is coupled to driven cam 416 and brush head support 419. Spring-like member 431, attached to driven cam 416, after a time becomes fully extended, moving in groove 452. When the peak 433 of driven cam 416 is passed by driving cam 414, as shown in dash-dot lines in FIG. 17c, spring-like member 431 springs back causing driven cam 416 to return to its rest position illustrated in solid lines in FIG. 17c. Driving shaft 412 then continues its rotational cycle in the direction of arrow 413 until the pushing and springing back of driven cam 416 is completed.

As driven cam 416 repeatedly returns to its rest position, brush head support 419 rotates in the direction indicated by arrow 434, resulting in the desired reciprocating motion of brush head 429.

Figure 18:
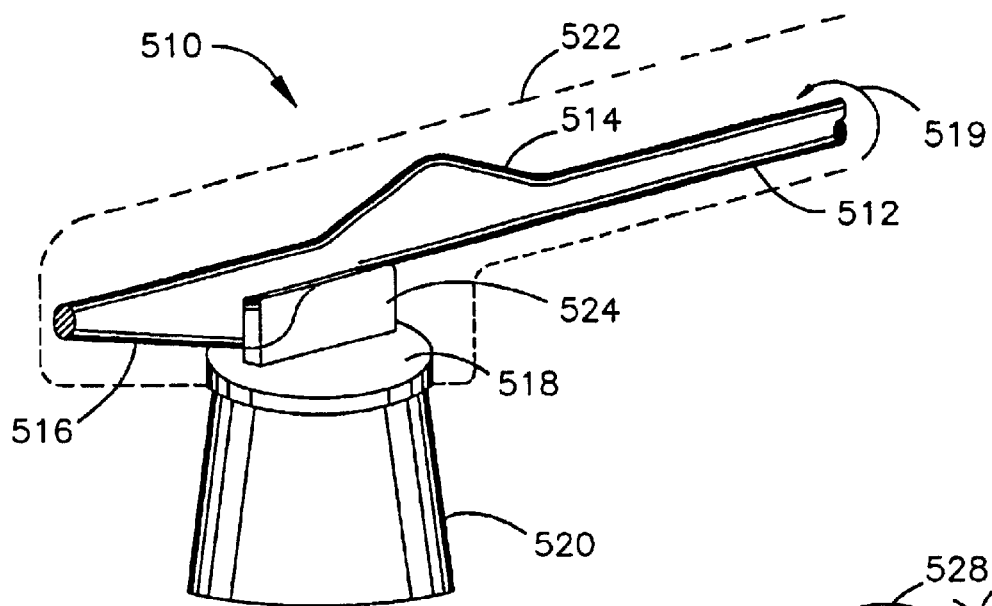
FIG. 18 is a perspective view of a plastic driving mechanism of the tool assembly incorporating a lobed member.
Figure 19:
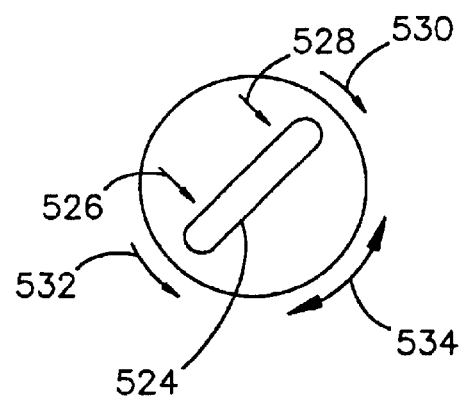
FIG. 19 is a top view of the tool assembly of FIG. 18.
Figure 20:
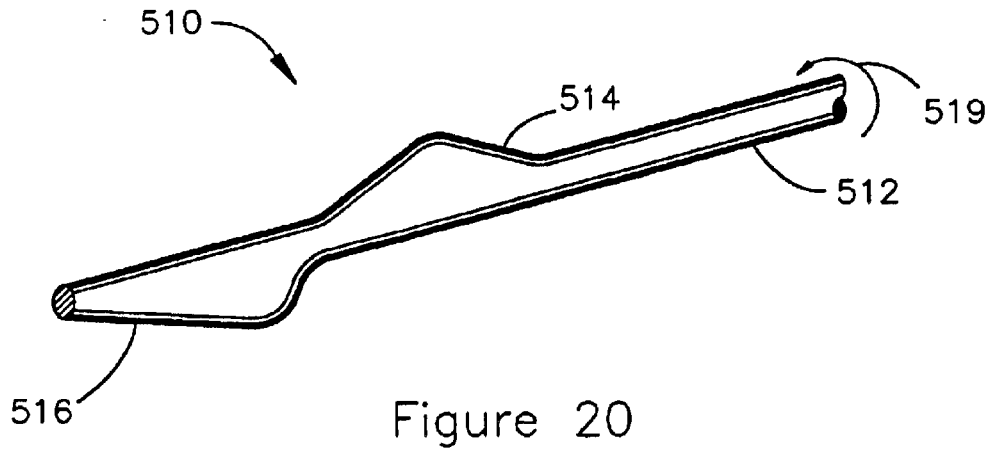
FIG. 20 is a perspective view of the lobed member of FIG. 18.

Turning to FIGS. 18–20, still yet another mechanism for achieving reciprocating movement in a brush head is illustrated. In this embodiment, reciprocating motion is achieved in the inventive plastic driving mechanism 510 by applying rotary motion to a lobed member 512. Lobed member 512 includes a pair of lobes 514 and 516. As lobed member 512 rotates in the direction of arrow 519, lobes 514 and 516 follow circular paths but are separated from each other by 180 degrees. In a fashion similar to that of the previous embodiments, a brush head support 518 on which a brush head 520 is mounted, is supported for reciprocating motion within a housing 522. Brush head support 518 includes an elongated cam follower 524 which is alternately acted on by lobe 514 in the direction of arrow 526, and then by lobe 516 in the direction indicated by arrow 528.

More particularly, when lobe 514 bears against elongated cam follower 524, brush head support 518 is moved in the direction indicated by arrow 530. Alternatively, when lobe 516 bears against elongated cam follower 524, brush head support 518 is moved in the direction indicated by arrow 532. The result of this alternating action is the desired inventive reciprocating motion indicated by arrow 534, as illustrated in FIG. 19.

Figure 21:
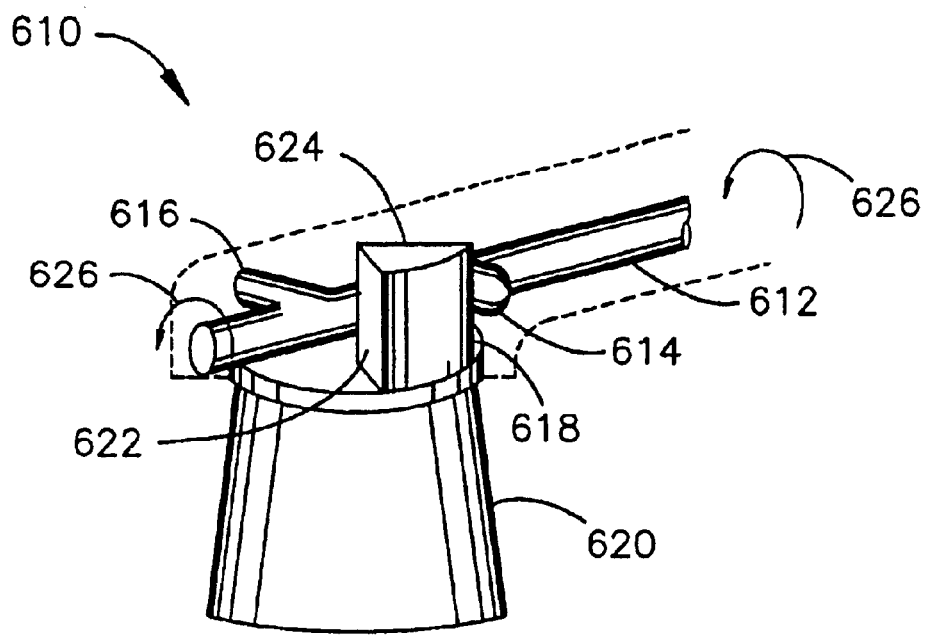
FIG. 21 is a perspective view of a plastic driving mechanism of the tool assembly incorporating a wedge-shaped member.
Figure 22:
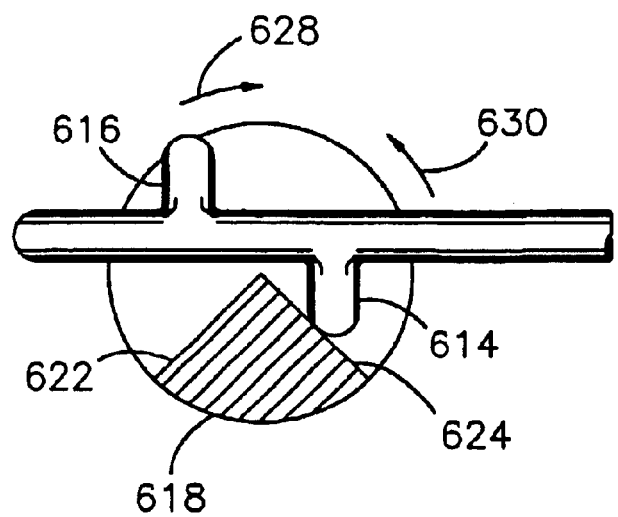
FIG. 22 is a top view of the tool assembly of FIG. 21.

Turning to FIGS. 21–22, reciprocating motion is achieved through the use of a wedge-shaped member attached to the support. More particular, the inventive plastic driving mechanism 610 comprises a rotating shaft 612 which has a pair of studs 614 and 616 attached to it. A wedge-shaped member 618 is secured to the top of support 620. Wedge-shaped member 618 includes a pair of side wedge surfaces 622 and 624. As shaft 612 rotates in the direction of arrow 626, alternatively stud 616 bears against surface 624, driving it in the direction of arrow 628, followed by stud 614 bearing against surface 624 driving it in the direction of arrow 630.

Figure 23:
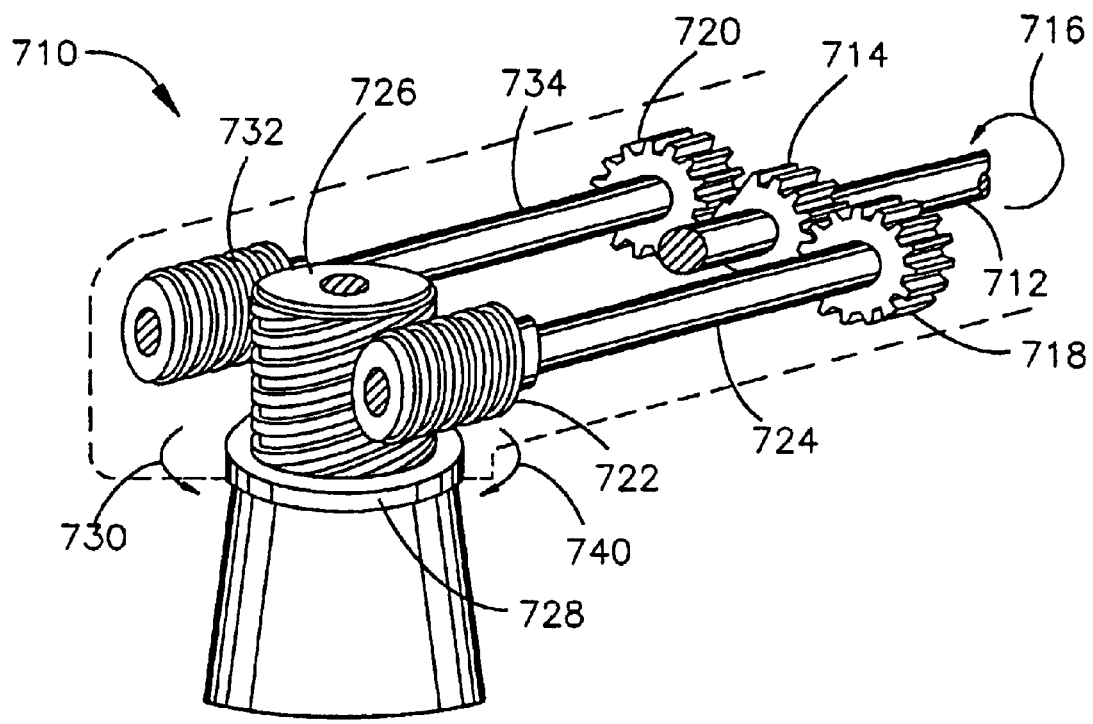
FIG. 23 is a perspective view of a plastic driving mechanism of the tool assembly incorporating a multiple gear driving mechanism.
Figure 24:
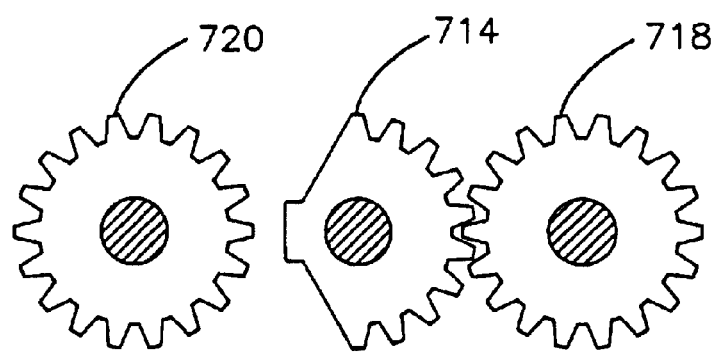
FIG. 24 is a cross-sectional view of the tool assembly of FIG. 23 along lines 24 showing the engagement of the driving surfaces of partial gear and follower toothed gears.

In accordance with the present invention, it is also contemplated that gears may be used to achieve reciprocating motion in a tool driven by a rotary power source. Referring to FIGS. 23–24, an inventive plastic driving mechanism 710 is provided with an input shaft 712 which is rotated, thus rotating a partial gear 714 which comprises about 75 degrees of a circular gear and has the appearance of a pie slice. As input shaft 712 is rotated in the direction of arrow 716, partial toothed gear 714 alternately engages smaller follower toothed gears 718 and 720 for a short period of time in the overall cycle of rotation of shaft 712.

When follower toothed gear 718 is rotated, it rotates worm gear 722 to which it is attached by coupling shaft 724. This results in worm gear 722 engaging gear 726, causing gear 726 and brush head support 728 to which it is secured, to rotate in the direction of arrow 730.

Similarly, when follower toothed gear 720 is rotated, it rotates worm gear 732 to which it is attached by coupling shaft 734. This results in worm gear 732 engaging gear 726, causing gear 726 and brush head support 728 to rotate in the direction of arrow 740.

Figure 25:
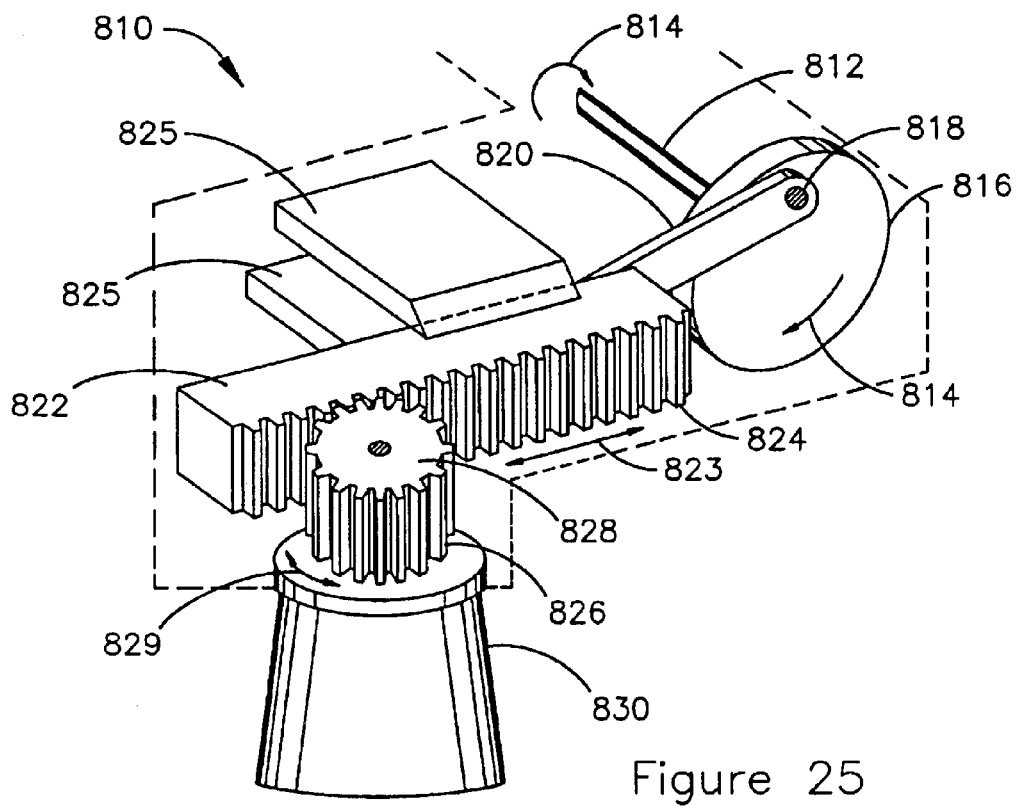
FIG. 25 is a perspective view of a plastic driving mechanism of the tool assembly incorporating a rack and pinion driving mechanism.

Referring to FIG. 25, yet another method for achieving the inventive reciprocating motion in a plastic driving mechanism 810 constructed in accordance with the present invention. In accordance with this embodiment, a drive shaft 812 is rotated in the direction indicated by arrow 814. This results in rotating disk 816 in the same direction. A pin 818 is mounted on disk 816. As disk 816 rotates, pin 818 follows a circular path. The result is to impart a reciprocating motion to coupling member 820 which is coupled to a rack 822 having a plurality of teeth 824 on it. Rack 822 is supported for sliding movement in the direction indicated by arrow 823 between a pair of support members 825. In this manner, rack 822 is given a reciprocating motion. Teeth 824 mesh with teeth 826 on pinion 828, causing reciprocating motion in pinion 828. The result is to achieve the desired reciprocating motion as indicated by arrow 829 in brush head support 830.

Figure 27:
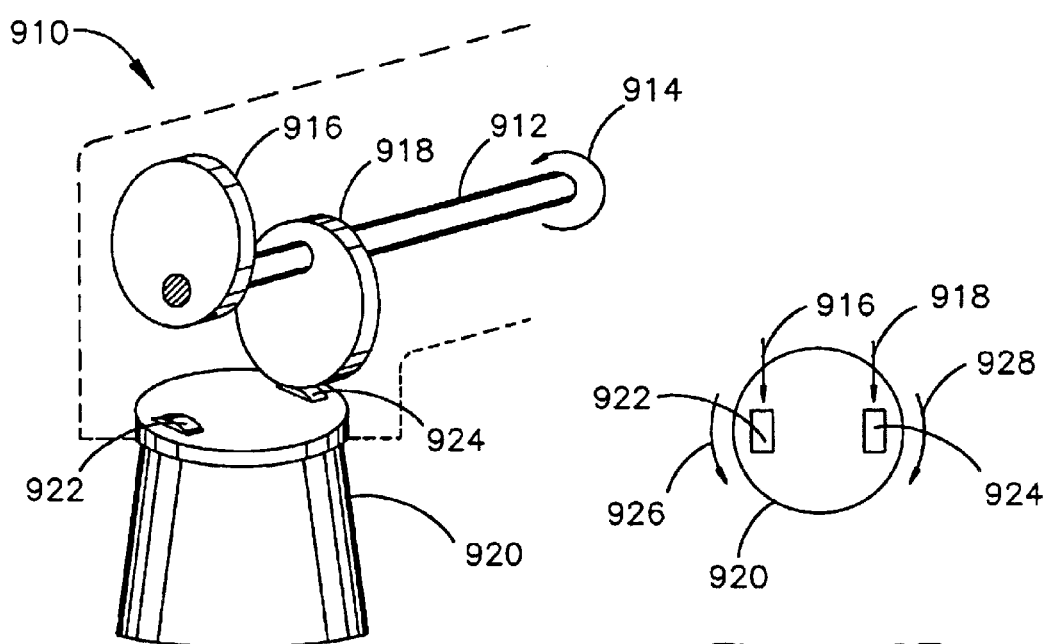
FIG. 27 is a top view of the tool assembly in FIG. 26.

Turning next to FIGS. 26 and 27, yet another mechanism for achieving reciprocating motion is shown. Here the inventive reciprocating plastic driving mechanism 910 is driven by a drive shaft 912 with rotary motion in the direction of arrow 914. At the end of drive shaft 912 are a pair of cams 916 and 918. Brush head support 920 includes a pair of cams 922 and 924. When cam 916 bears against cam 922 it urges brush head support 920 in the direction indicated by arrow 926. Similarly, when cam 918 bears against cam 924 it urges brush head support 920 in the direction indicated by arrow 928. Because cams 916 and 918 are positioned on shaft 912 at 180 degrees with respect to each other, they are bearing against cams 922 and 924 at different times, and this causes reciprocating motion in brush head support 920.

Still yet another approach is illustrated in FIGS. 28 and 29. In this embodiment, power is provided to the inventive reciprocating plastic driving mechanism 1010 by a drive shaft 1012 which is rotated in the direction of arrow 1014. The end of shaft 1012 has a pair of partial pie-shaped toothed gears 1016 and 1018 which have teeth that mesh with teeth on a conical gear 1020.

As can be seen in FIG. 28, as shaft 1012 rotates, gear 1018 causes follower gear 1020 to rotate in the direction of arrow 1022 when the teeth of gear 1020 engage gear 1018. At other times, when the teeth of gear 1016 engage the teeth of gear 1020, gear 1020 is caused to rotate in the direction indicated by arrow 1024, resulting in reciprocating motion of gear 1020 and brush head support 1026.

Referring to FIG. 30, an electromechanical approach to the problem of providing reciprocating motion by an inventive reciprocating plastic driving mechanism 1120 is illustrated. The same may be done using an electromechanical operator 1112 to directly provide reciprocating motion. Alternatively, a simpler electromechanical operator may be used which only provides for movement in one direction, with movement in the opposite direction being provided by a spring biased arrangement of the type illustrated and described in connection with FIG. 17, above.

Figure 31:
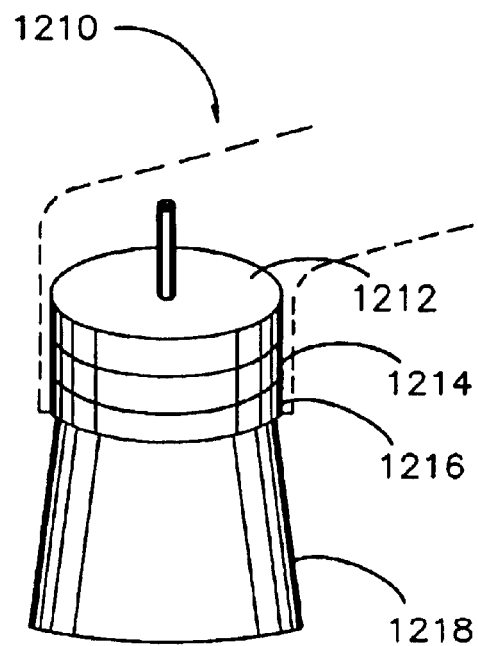
FIG. 31 is a perspective view of a plastic driving mechanism of the tool assembly incorporating a magnetic-mechanically coupled multiple clutch driving mechanism.

Turning next to FIG. 31, in accordance with the present invention it is contemplated that magnetic coupling may be used to relieve the stress applied to the gums during continuous motion. Such a magnetic coupling may simply comprise a magnetic clutch. In particular, the inventive reciprocating plastic driving mechanism 1210 is provided with a driving clutch member 1212 which is magnetically coupled to a driven clutch member 1214 to achieve a magnetic-mechanical connection between the two magnet members.

Driving clutch member 1212 and driven clutch member 1214 may also be made of plastic, as such materials are inexpensive and widely available. As alluded to above, the invention contemplates the fabrication of all the embodiments of the invention in plastic, although substitution of other materials is possible. In any case, the inventive structures are configured in a manner that provides for durability, even in relatively inexpensive and weak plastic materials.

When driving clutch member 1212 is rotated, a driven clutch member 1214 is caused to rotate because of the magnetic-mechanical connection, thus resulting in a transfer of power. Clutch member 1214, in turn, is coupled to the brush head support 1216 in order to rotate the brush head 1218. Such a magnetic clutch will release if tension applied to the gums becomes too great. Such a mechanism can be used in combination with any of the reciprocating plastic driving mechanisms described in this application to achieve an additional measure of protection. In addition, magnetic coupling may be used in place of the various forms of mechanical coupling to achieve the desired reciprocating motion in the various embodiments disclosed herein.

Figure 32:
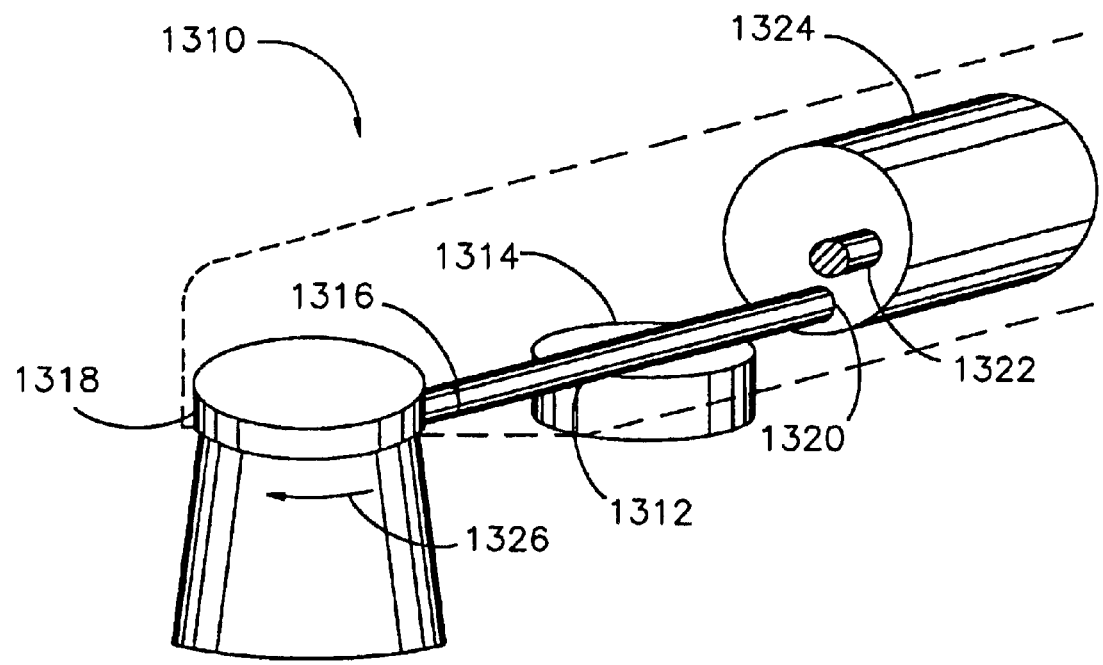
FIG. 32 is a perspective view of a plastic driving mechanism of the tool assembly incorporating a spring like driving mechanism.

Turning next to FIG. 32, still yet another approach is illustrated. In accordance with this approach, a reciprocating plastic driving mechanism 1310 includes a plastic spring like member 1312 mounted for rotation on a support 1314 and coupled by a living hinge 1316 to a brush head support 1318 as illustrated. The far end 1320 of the spring like member 1312 is acted on by a stud 1322 mounted on a rotating member 1324. When rotating member 1324 rotates, stud 1322 impacts far end 1320, causing the other end to displace the position of living hinge 1316 causing movement of brush head support 1318 in the direction indicated by arrow 1326. Because member 1312 is a spring, when the impact is over, brush head support 1318 moves in the opposite direction, thus resulting in reciprocating motion.

Figure 33:
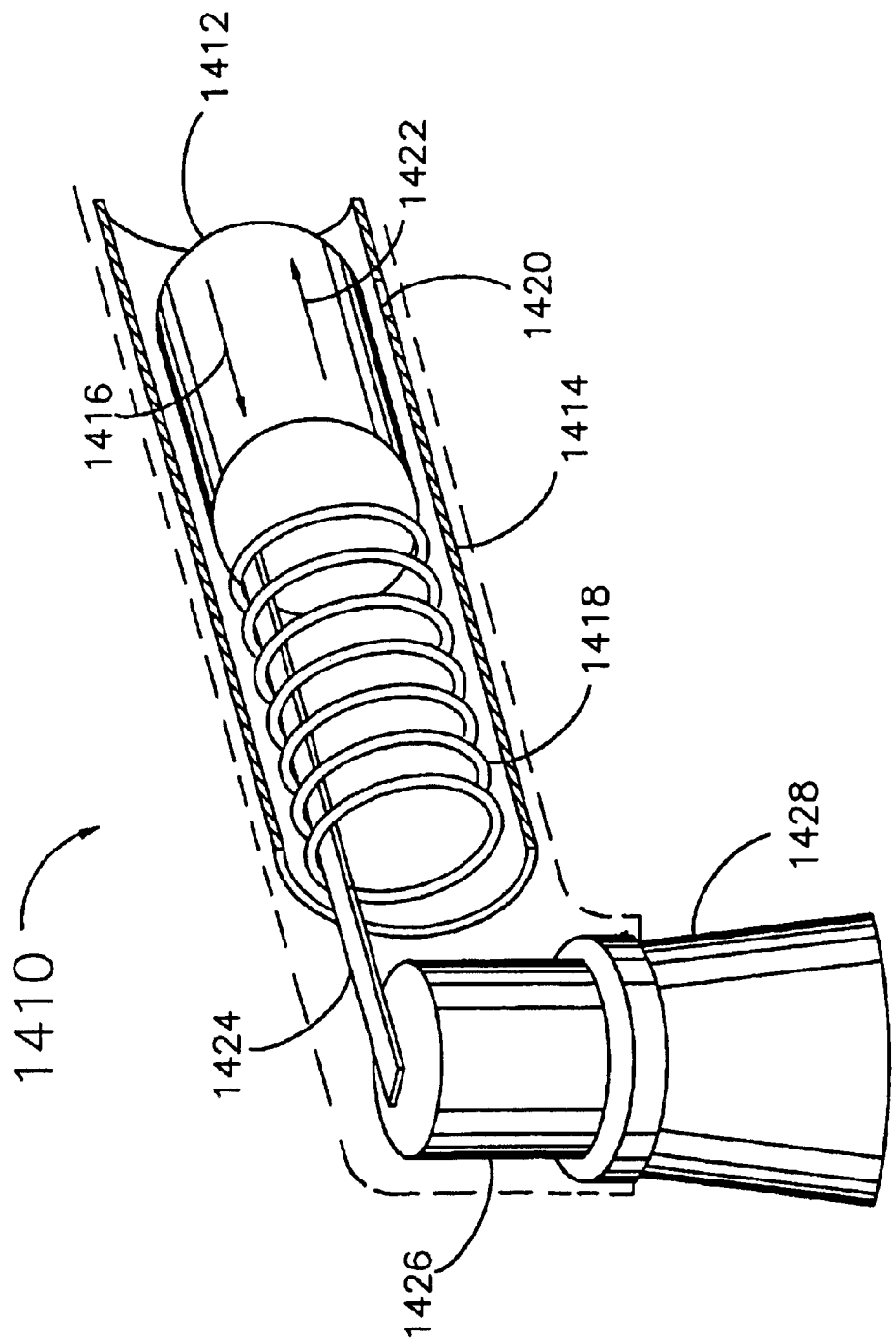
FIG. 33 is a perspective view of a plastic driving mechanism of the tool assembly incorporating a piston driving mechanism.

Turning to FIG. 33, because tools often have air pressure as a primary source of power, using a converter which converts air pressure into rotary motion, the possibility also exists to achieve reciprocating motion from air pressure directly. The same can be achieved in a reciprocating plastic driving mechanism 1410 by a number of means, including the use of a piston 1412 in a cylinder 1414. The air pressure drives the piston 1412 in the direction indicated by arrow 1416 against the action of a spring 1418 which is compressed by the movement of the piston 1412. Pressure maybe released by a vent 1420 causing spring 1418 to push the piston 1412 back in the direction indicated by arrow 1422. Piston 1412 is coupled by link 1424 to a brush head support 1426. The result is that link 1424 couples the reciprocating motion to brush head support 1426 resulting in reciprocating motion of brush head 1428.

Figure 34:
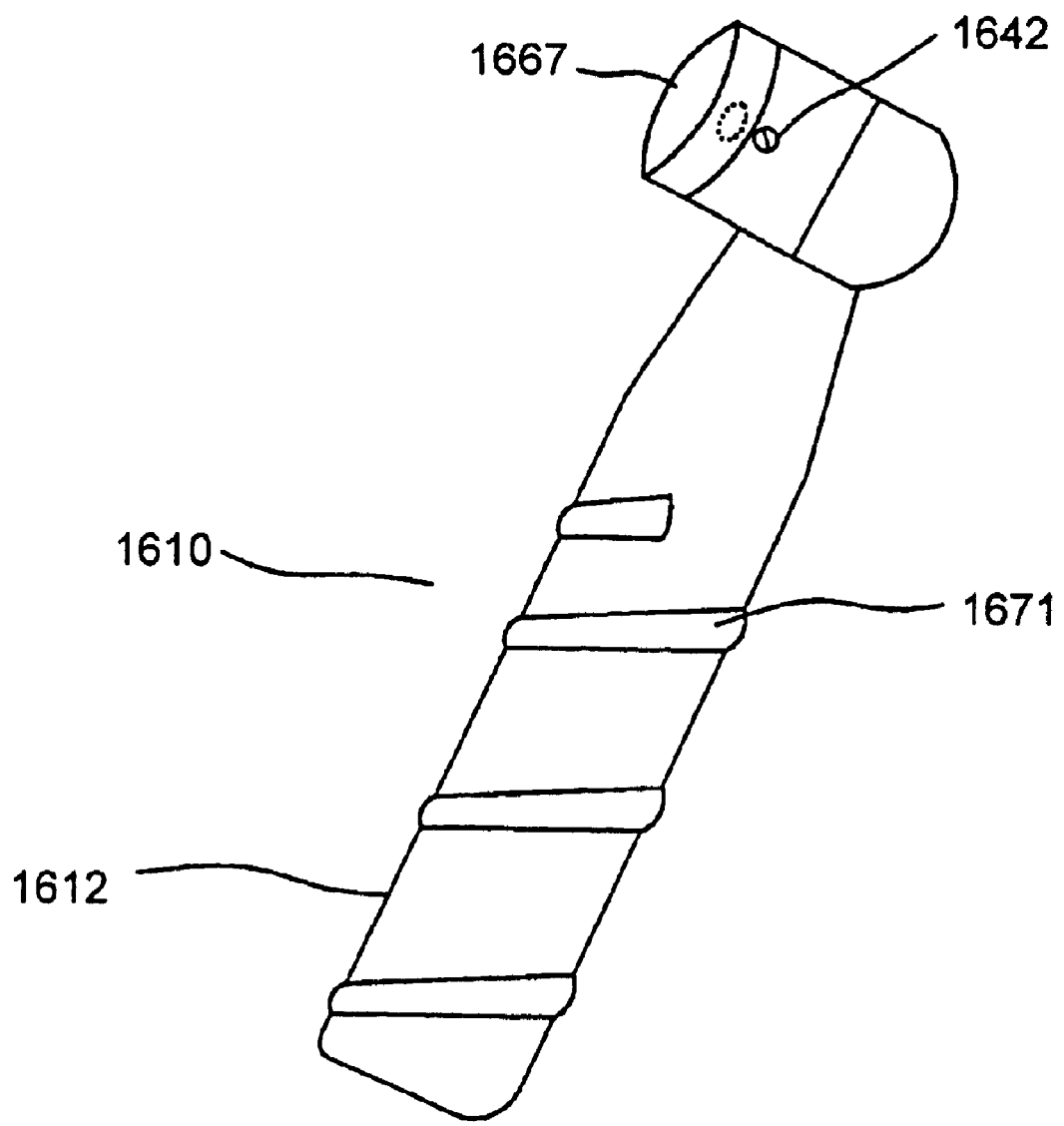
FIG. 34 is an elevational, side view of a dermabrasion tool assembly with an abrasive head attached to the coupling element in accordance with the principles of the present invention.

In an alternative embodiment in accordance with the invention shown in FIG. 34, a reciprocating polishing device 1610 for buffing nails is provided for a safer and more effective solution. Polishing device 1610 similar to the embodiments described above includes a housing 1612. Housing 1612 also includes a raised portion 1671 extending outwardly from its outer surface and is preferably integral therewith. Raised portion 1671 is sized and positioned to aid a user in gripping polishing device 1610, which may include a single or multiple spiral arrangement. Since device 1610 only reciprocates, it will not cut into a cuticle and thus would work effectively even in the hands of the novice nail salon manicurist. A modified standard prophy cup is coupled to coupling element 1642 which has an abrasive pad or polishing pad 1667 glued on to its surface. The operation of the system is substantially identical to the systems described in the previous figures. In preferred embodiments, different grades of abrasives or different polishing discs could be attached as needed with disposable heads. In an alternative embodiment, instead of a rubber cup, different polishing discs would be attached and a liquid abrasive would be injected that would dry and then be used by the nail salons. In a preferred embodiment, the attachments would be disposable for each customer.

Figure 35:
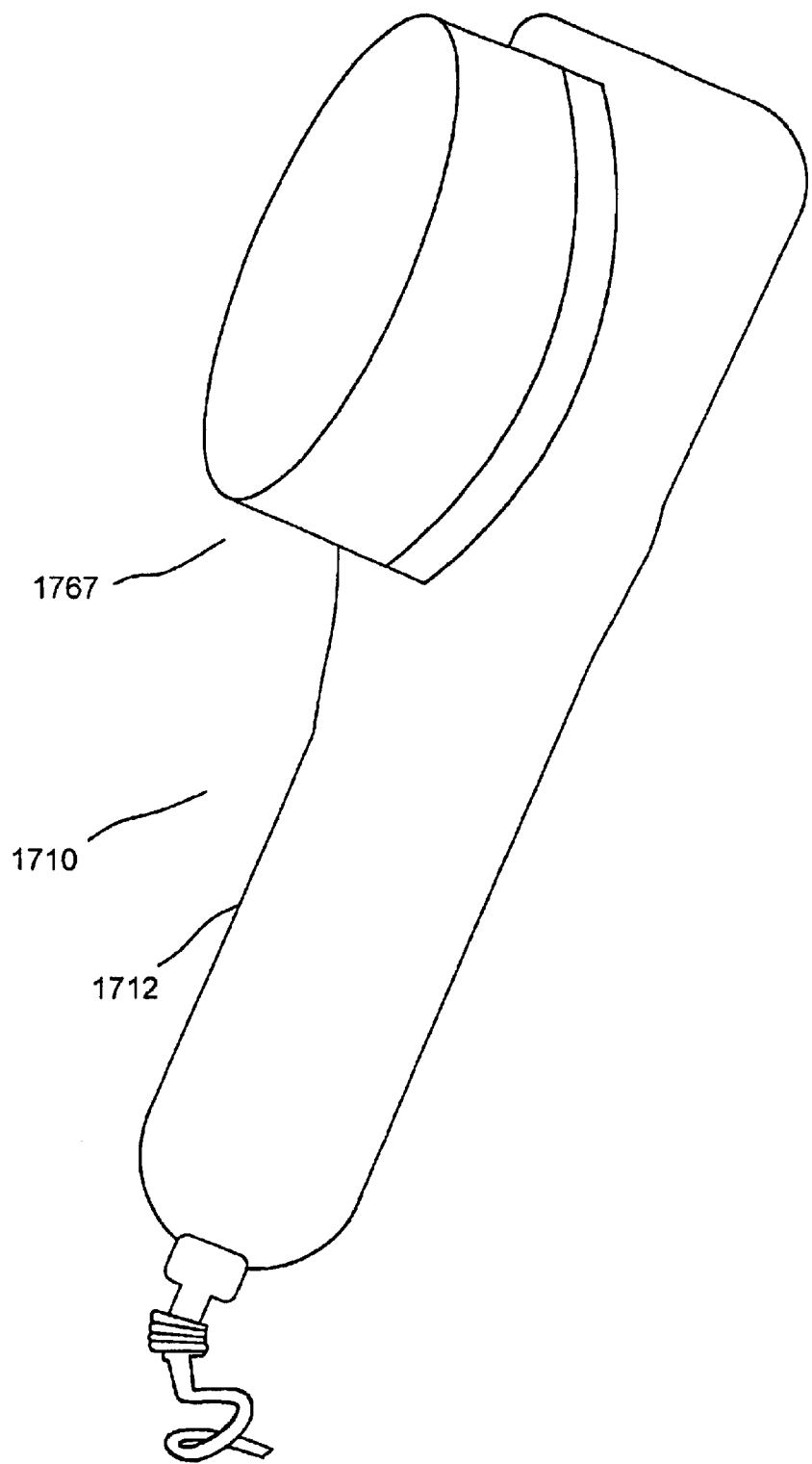
FIG. 35 is an elevational, side view of a sanding tool assembly with a sanding surface attached to the coupling element in accordance with the principles of the present invention.

In an alternative embodiment in accordance with the invention shown in FIG. 35, a sanding device 1710 for sanding wood and including a sander pad 1767 on the reciprocating head is illustrated. The operation of the system is substantially identical to the systems illustrated in the previous figures. An alternative embodiment has a rotary electrical motor directly coupled to the cam driver and drives the cam to execute a reciprocating movement. It is also contemplated that this device modified with a brush attachment, will be useful for applying polish to wood, leather and similar materials.

The inventive reciprocating motion converting head is also of particular value as a drive mechanism for other devices which are used to contact the body for skin dermabrasion techniques. Here again the use of reciprocal motion minimizes damage to the skin while achieving a good abrasive action with the use of an abrasive disk, or the use of a disk with an abrading compound.

Figure 36:
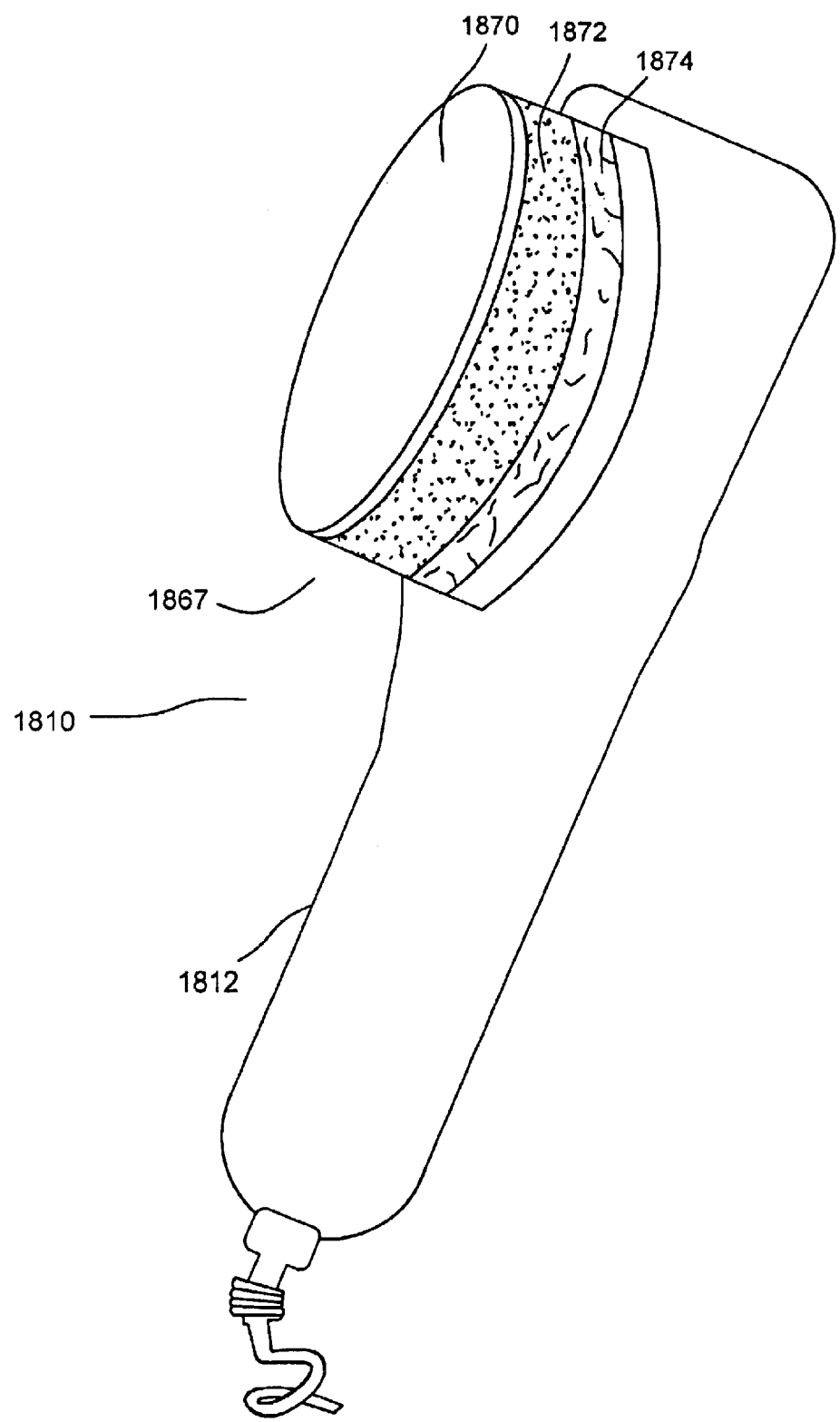
FIG. 36 is an elevational, side view of a facial tool assembly with a multi-layered surface attached to the coupling element in accordance with the principles of the present invention.

In an alternative embodiment in accordance with the invention shown in FIG. 36, a multiple task facial device 1810 is shown. Instead of a sanding pad, the device has an attachment 1867 with three layers—similar to a layered soap. The outermost layer, layer 1870 is a thin layer of astringent to prepare the face for cleaning. The astringent may comprise layer 1870 or layer 1870 may comprise a piece of paper or another carrier with astringent which can then be peeled off. The central layer 1872 is an exfoliating layer where the surface comprises a packed set of exfoliating crystals and cleansers to clean and exfoliate the face. The innermost layer, layer 1874 is a moisturizing layer to soothe the face and comprises appropriate moisturizers. The device has the benefit of using prepackaged disposable discs for a complete facial system. There is less clean up and less chance for the products to become contaminated or rancid over time since a fresh disc is used every time. Additionally, one would not have to damage the delicate skin on one's fingers by applying exfoliant since the exfoliant would not be in contact with the user's hands. It is also contemplated that layer 1874 would comprise a absorbable material which would allow the user to inject the appropriate moisturizer. Similar arrangements are contemplated for treatment of problem skin, blackheads, and the like. It is also contemplated that multi-layer attachment 1867 could comprise appropriate materials for furniture preparation, or treatment of other surfaces that would benefit from the use of reciprocal motion.

While the foregoing description and drawings represent the preferred embodiments of the present invention, it will be understood that various additions, modifications and substitutions may be made without departing from the spirit and scope of the present invention as defined in the accompanying claims. In particular, it will be clear that the present invention may be embodied in other specific forms, structures, arrangements, proportions, and with other elements, materials, and components, without departing from the spirit or essential characteristics thereof.

What is claimed is:

1. A manicure tool for shaping and smoothing nails having a transmission for changing rotary motion into angularly reciprocating motion and adapted to be mounted on the output end of a power unit of the type having a rotary drive output and used to drive the manicure tool, said transmission comprising:
   (a) a support member (42);
   (b) a driving member (30) in a first plane oriented in a first direction supported by said support member (42) for rotary motion;
   (c) a driven member (40) made of a resinous material and supported by said support member (42) for reciprocating angular movement by said support member (42) in a second plane, said second plane being transverse to said first plane, said driving member (30), said driven resinous member (40) and said support member (42) forming a transmission subassembly adapted to be mounted on the output end of said power unit with said rotary drive output mechanically coupled to said driving member (30);
   (d) a driving cam surface (50) disposed on a portion of said driving member (30), said driving cam surface (50) having a first shape;
   (e) a driven cam surface (60) disposed on a portion of said driven resinous member (40), said driven cam surface (60) having a second shape, said driven resinous member (40) being supported with respect said driving member (30) in a position where said driving cam surface (50) is in contact with said driven cam surface (60) during at least a portion of the cycle of rotation of said driving cam surface (50), said second shape configured and dimensioned to be driven by said driving cam surface (50) in a positive angular direction during one part of said cycle and be driven by said driving cam surface (50) in a negative angular direction during another part of said cycle wherein said driven cam surface (60) comprises a shaft mounted onto a support, wherein the support is coupled to a coupling element having a pad attached to the surface of the coupling element.

2. A manicure tool according to claim 1 wherein the coupling element is a disposable head having a disc with an abrasive surface.

3. A manicure tool kit comprising the manicure tool according to claim 1 and further comprising a plurality of coupling elements wherein each of the coupling elements is a disposable head having a disc with an abrasive surface wherein at least one of the heads has a disc having a surface suitable for filing fingernails, at least one of the heads has a disc having a surface suitable for filing toenails, at least one of the heads has a disc having a surface suitable for buffing fingernails, at least one of the heads has a disc having a surface suitable for polishing fingernails.

4. A manicure tool kit comprising the manicure tool according to claim 1 and further comprising a plurality of coupling elements wherein each of the coupling elements is a reusable head having a disc with an abrasive surface wherein at least one of the heads has a disc having a surface suitable for filing fingernails, at least one of the heads has a disc having a surface suitable for filing toenails, at least one of the heads has a disc having a surface suitable for buffing fingernails, at least one of the heads has a disc having a surface suitable for polishing fingernails.

5. A polishing tool having a transmission for changing rotary motion into angularly reciprocating motion and adapted to be mounted on the output end of a power unit of the type having a rotary drive output and used to drive the body polishing tool, said transmission comprising:
(a) a support member (42);
(b) a driving member (30) in a first plane oriented in a first direction supported by said support member (42) for rotary motion;
(c) a driven member (40) made of a resinous material and supported by said support member (42) for reciprocating angular movement by said support member (42) in a second plane, said second plane being transverse to said first plane, said driving member (30), said driven resinous member (40) and said support member (42) forming a transmission subassembly adapted to be mounted on the output end of said power unit with said rotary drive output mechanically coupled to said driving member (30);
(d) a driving cam surface (50) disposed on a portion of said driving member (30), said driving cam surface (50) having a first shape;
(e) a driven cam surface (60) disposed on a portion of said driven resinous member (40), said driven cam surface (60) having a second shape, said driven resinous member (40) being supported with respect said driving member (30) in a position where said driving cam surface (50) is in contact with said driven cam surface (60) during at least a portion of the cycle of rotation of said driving cam surface (50), said second shape configured and dimensioned to be driven by said driving cam surface (50) in a positive angular direction during one part of said cycle and be driven by said driving cam surface (50) in a negative angular direction during another part of said cycle wherein said driven cam surface (60) comprises a shaft mounted onto a support, wherein the support is coupled to a coupling element having a pad attached to the surface of the coupling element wherein the coupling element is a disposable head having a polishing disc with an abrasive surface.

6. A polishing tool according to claim 5 wherein the tool is a body polishing tool wherein the coupling element is a disposable head having a polishing disc with an abrasive surface.

7. A body polishing tool according to claim 6 wherein the polishing disc further comprises a skin abraiding compound.

8. A polishing tool according to claim 5 wherein the polishing brush may be replaced with a soft cloth surface.

9. A polishing tool according to claim 5 wherein the polishing brush comprises polishing cream.

10. A sanding tool for sanding surfaces having a transmission for changing rotary motion into angularly reciprocating motion and adapted to be mounted on the output end of a power unit of the type having a rotary drive output and used to drive the sanding tool, said transmission comprising:
(a) a support member (42);
(b) a driving member (30) in a first plane oriented in a first direction supported by said support member (42) for rotary motion;
(c) a driven member (40) made of a resinous material and supported by said support member (42) for reciprocating angular movement by said support member (42) in a second plane, said second plane being transverse to said first plane, said driving member (30), said driven resinous member (40) and said support member (42) forming a transmission subassembly adapted to be mounted on the output end of said power unit with said rotary drive output mechanically coupled to said driving member (30);
(d) a driving cam surface (50) disposed on a portion of said driving member (30), said driving cam surface (50) having a first shape;
(e) a driven cam surface (60) disposed on a portion of said driven resinous member (40), said driven cam surface (60) having a second shape, said driven resinous member (40) being supported with respect said driving member (30) in a position where said driving cam surface (50) is in contact with said driven cam surface (60) during at least a portion of the cycle of rotation of said driving cam surface (50), said second shape configured and dimensioned to be driven by said driving cam surface (50) in a positive angular direction during one part of said cycle and be driven by said driving cam surface (50) in a negative angular direction during another part of said cycle wherein said driven cam surface (60) comprises a shaft mounted onto a prophy angle support, wherein the prophy angle support is coupled to a coupling element having a pad attached to the surface of the coupling element wherein the coupling element is a disposable head having a sanding disc with an abrasive surface suitable for sanding.

11. A sanding tool according to claim 10 wherein the disc is disposable.

12. A transmission for changing rotary motion into angularly reciprocating motion and adapted to be mounted on the output end of a power unit of the type having a rotary drive output and used to drive a tool, said transmission comprising:
(a) a support member;
(b) a driving member made of a resinous material and supported by said support member for rotary motion;
(c) a driven member made of a resinous material and supported by said support member for reciprocating angular movement by said support member, said driving resinous member, said driven resinous member and said support member forming a transmission subassembly adapted to be mounted on the output end of said power unit with said rotary drive output mechanically coupled to said driving resinous member;
(d) a driving cam surface disposed on a portion of said driving resinous member, said driving cam surface having a first shape;

(e) a driven cam surface disposed on a portion of said driven resinous member, said driven cam surface having a second shape, said driven resinous member being supported with respect said driving resinous member in a position where said driving cam surface is in contact with said driven cam surface during at least a portion of the cycle of rotation of said driving cam surface, said second shape configured and dimensioned to be driven by said driving cam surface in a positive angular direction during one part of said cycle and is driven by said driving cam surface in a negative angular direction during another part of said cycle.

* * * * *